United States Patent
Veiner

(10) Patent No.: US 11,940,459 B2
(45) Date of Patent: *Mar. 26, 2024

(54) DILUENT PREPARATION MODULE

(71) Applicant: Beckman Coulter, Inc., Brea, CA (US)

(72) Inventor: Craig R Veiner, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/531,519

(22) Filed: Nov. 19, 2021

(65) Prior Publication Data

US 2022/0155330 A1    May 19, 2022

Related U.S. Application Data

(60) Continuation of application No. 17/123,797, filed on Dec. 16, 2020, now Pat. No. 11,209,451, which is a
(Continued)

(51) Int. Cl.
*G01N 35/10*     (2006.01)
*G01N 1/38*      (2006.01)
(Continued)

(52) U.S. Cl.
CPC .......... *G01N 35/1016* (2013.01); *G01N 1/38* (2013.01); *G01N 33/5008* (2013.01);
(Continued)

(58) Field of Classification Search
CPC .......... G01N 35/1016; G01N 35/1002; G01N 35/00693; G01N 1/38; G01N 2001/383;
(Continued)

(56) References Cited

U.S. PATENT DOCUMENTS

| 4,804,519 A | 2/1989 | Sainz et al. |
| 5,428,993 A | 7/1995 | Kobashi |

(Continued)

FOREIGN PATENT DOCUMENTS

| CN | 1675529 | 9/2005 |
| CN | 1675530 | 9/2005 |

(Continued)

OTHER PUBLICATIONS

"U.S. Appl. No. 16/198,366, Notice of Allowance dated Sep. 23, 2020", 11 pgs.

(Continued)

*Primary Examiner* — Lessanework Seifu
(74) *Attorney, Agent, or Firm* — Schwegman Lundberg & Woessner, P.A.

(57) ABSTRACT

Certain types of automated medical analysis equipment are used to analyze blood or other fluids. The equipment may thus use various diluents or reagents that allow the blood or other fluids to be run through the analysis equipment for analysis and data collection. Disclosed is a diluent preparation module that combines purified water and reagent concentrate for use by this equipment. Also disclosed is a diluent preparation unit that combines more than one diluent preparation modules for redundancy and back-up purposes. Also disclosed are systems for supplying the Diluent prepared by the diluent preparation module or diluent preparation unit to one or more analytic instruments.

20 Claims, 12 Drawing Sheets

Related U.S. Application Data division of application No. 16/198,366, filed on Nov. 21, 2018, now Pat. No. 10,900,984.

(60) Provisional application No. 62/589,563, filed on Nov. 22, 2017, provisional application No. 62/589,561, filed on Nov. 22, 2017, provisional application No. 62/589,557, filed on Nov. 22, 2017.

(51) Int. Cl.
  *G01N 33/50* (2006.01)
  *G01N 33/53* (2006.01)
  *G01N 35/00* (2006.01)

(52) U.S. Cl.
  CPC ..... *G01N 35/1002* (2013.01); *G01N 2001/383* (2013.01); *G01N 33/5302* (2013.01); *G01N 35/00693* (2013.01); *G01N 2035/1058* (2013.01)

(58) Field of Classification Search
  CPC ...... G01N 2001/386; G01N 2035/1058; B01F 3/08; B01F 5/00
  See application file for complete search history.

(56) References Cited

U.S. PATENT DOCUMENTS

| | | | |
|---|---|---|---|
| 5,800,056 A * | 9/1998 | Suzuki | B01F 35/81 137/5 |
| 7,469,606 B1 | 12/2008 | Wiederin | |
| 8,158,601 B2 | 4/2012 | Chen et al. | |
| 8,191,397 B2 * | 6/2012 | Doniat | G01N 27/06 73/1.03 |
| 9,164,021 B2 | 10/2015 | Okubo et al. | |
| 10,900,984 B2 | 1/2021 | Veiner | |
| 11,209,451 B2 | 12/2021 | Veiner | |
| 2002/0175183 A1 * | 11/2002 | Schell | B01F 23/49 222/424.5 |
| 2006/0014270 A1 | 1/2006 | Månsson et al. | |
| 2006/0121624 A1 | 6/2006 | Huang et al. | |
| 2012/0301359 A1 | 11/2012 | Kraemer et al. | |
| 2016/0124008 A1 | 5/2016 | Kraemer et al. | |
| 2019/0154718 A1 | 5/2019 | Veiner | |
| 2021/0102967 A1 | 4/2021 | Veiner | |

FOREIGN PATENT DOCUMENTS

| | | |
|---|---|---|
| CN | 101040041 | 9/2007 |
| CN | 101909755 | 12/2010 |
| CN | 203275172 | 11/2013 |
| CN | 101816907 | 4/2016 |
| CN | 105628482 | 6/2016 |
| EP | 2224247 A2 | 9/2010 |
| EP | 2233929 A2 | 9/2010 |
| EP | 2400305 A1 | 12/2011 |
| JP | 5384671 B2 | 10/2013 |
| WO | WO-2019104198 A2 | 5/2019 |
| WO | WO-2019104198 A3 | 6/2019 |

OTHER PUBLICATIONS

"U.S. Appl. No. 16/198,366, Response filed Jul. 20, 2020 to Restriction Requirement dated May 19, 2020", 9 pgs.
"U.S. Appl. No. 16/198,366, Restriction Requirement dated May 19, 2020", 6 pgs.
"U.S. Appl. No. 17/123,797, Notice of Allowance dated Aug. 23, 2021", 7 pgs.
"Global Leader in Automated Hematology Diagnostics", SYSMEX Hematology Overview, [Online] Retrieved from the Internet: <URL: https://www.sysmex.com/us/en/products/hematology/Pages/sysmex-Hematology-Overview.aspx>, (Nov. 2, 2018), 2 pgs.
"International Application Serial No. PCT/US2018/062286, International Search Report dated May 28, 2019", 7 pgs.
"International Application Serial No. PCT/US2018/062286, Invitation to Pay Additional Fees dated Feb. 27, 2019", 13 pgs.
"International Application Serial No. PCT/US2018/062286, Written Opinion dated May 28, 2019", 13 pgs.
"Chinese Application Serial No. 201880075769.6, Office Action dated Feb. 10, 2023", w machine translation, 32 pgs.
"Chinese Application Serial No. 201880075769.6, Response filed Jun. 21, 2023 to Office Action dated Feb. 10, 2023", w english claims, 14 pgs.

\* cited by examiner

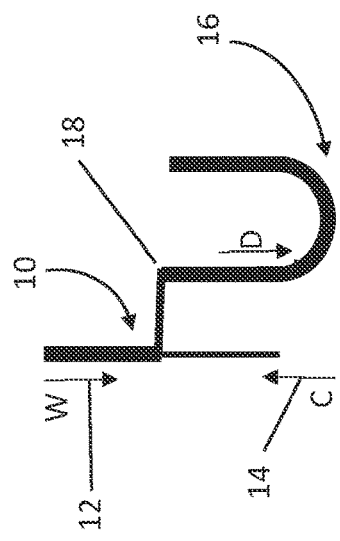
Fig. 1
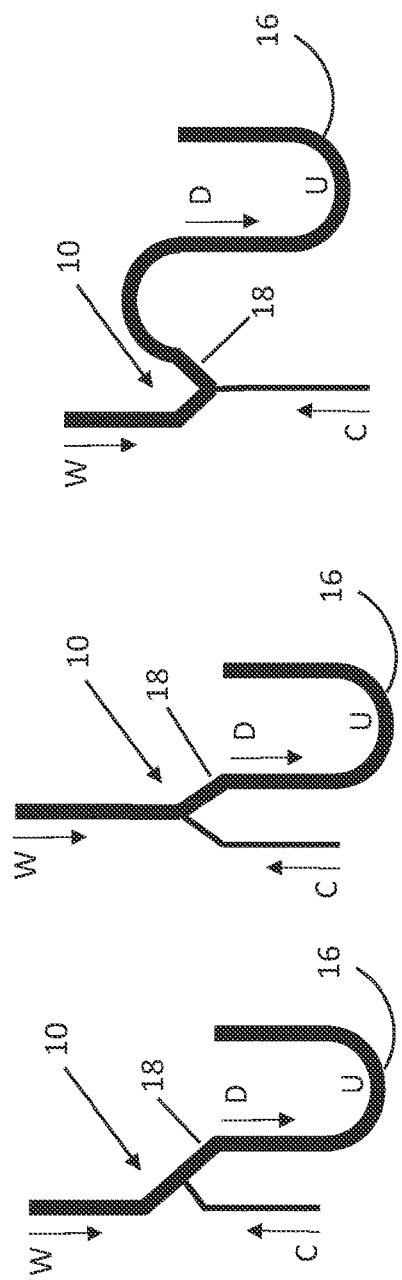
Fig. 2A
Fig. 2B
Fig. 2C
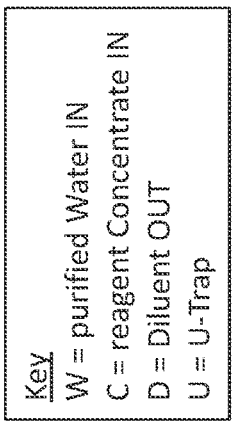
Key
W = purified Water IN
C = reagent Concentrate IN
D = Diluent OUT
U = U-Trap

DILUENT PREPARATION MODULE

CROSS REFERENCE TO RELATED APPLICATIONS

This application is a continuation of U.S. patent application Ser. No. 17/123,797, filed Dec. 16, 2020, which application is a division of U.S. patent application Ser. No. 16/198,366, filed Nov. 21, 2018, now issued as U.S. Pat. No. 10,900,984, which claims the benefit of U.S. Provisional Application Ser. No. 62/589,557, filed Nov. 22, 2017, titled "Diluent Preparation Module," U.S. Provisional Application Ser. No. 62/589,561, filed Nov. 22, 2017, titled "Diluent Preparation Unit including Two or More Diluent Preparation Modules," and U.S. Provisional Application Ser. No. 62/589,563, filed Nov. 22, 2017, titled "System for Using a Diluent Preparation Unit containing Two or More Diluent Preparation Modules with One or More Analytic Instruments," the entire contents of each of which are hereby incorporated by reference.

FIELD OF THE DISCLOSURE

Embodiments of the present disclosure relate generally to the field of automated medical analysis equipment and the fluids used therein. Certain types of automated medical analysis equipment are used to analyze blood or other fluids. The equipment may thus use various diluents or reagents that allow the blood or other fluids to be run through the analysis equipment for analysis and data collection. Disclosed is a diluent preparation module that combines purified water and reagent concentrate for use by this equipment. Also disclosed is a diluent preparation unit that combines more than one diluent preparation module for redundancy and back-up purposes. Also disclosed are systems for supplying the Diluent prepared by the diluent preparation module or diluent preparation unit to one or more analytic instruments.

BACKGROUND

During operation of automated medical analysis equipment such as various types of analytic instruments and laboratory equipment, it is often the case that the sample to be analyzed is mixed or combined with one or more reagents or diluents. This can help the sample to properly flow through the analytic equipment components for testing. For example, body fluid analyzers (such as hematology analyzers, urinalysis equipment, or other types of body fluid analyzers or instruments) may receive an input of the fluid to be tested and run various tests in order to collect accurate data about individual cell size, shape, structure, and count. These analyzers may operate via electrical impedance, flow cytometry, fluorescent flow cytometry, or various other methods. The analyzers are generally used in combination with one or more chemical reagents and/or diluents that lyse, assist and create cell flow, alter the cells of the body fluid to be analyzed, or any other function.

In one specific example, a Beckman Coulter Slide Maker Stainer and a Beckman Coulter Hematology Analyzer are both commercially available medical diagnostic equipment. This diagnostic equipment uses COULTER® DxH™ Diluent (which may be referred to herein as "Diluent"), a commercially available isotonic buffered Diluent in conjunction with a cyanide-free lytic agent for counting and sizing blood cells on the workcell. COULTER® DxH™ Diluent is currently provided in Ready-to-Use 10 L reagent packs. The DxH 2401 workcell uses Diluent at a rate of up to 17.4 liters per hour, requiring the user to replace a reagent pack about every 34 minutes. This means that pallets of reagent packs are often required to be stored close to workcells in order to keep up with demand.

Beckman Coulter Hematology Analyzers utilize the Coulter principle, which analyzes electrical impedance of individual cells to count and classify. The Diluent is an active component in the Coulter principle measurements. The Diluent also carries the cells through the system. Other analysis systems that rely on flowcytometric analysis (light) (for example, systems available from Sysmex, as described briefly below) use a system diluent predominantly as a carrier.

Sysmex® Corporation is a Japanese company headquartered in Kobe that is engaged in the health care business. Originally called TOA Medical Electronics (a branch of the TOA Corporation), the company was originally involved with hematology analyzers. Sysmex Corporation has an external diluter system that attaches to its hematology analyzers. The Sysmex hematology analyzers do not use Coulter Principle; instead, they use flowcytometric analysis (light) where the system diluent is predominantly a carrier.

European Granted Patent No. EP2233929B1 titled "Reagent preparing apparatus and sample analyzer" assigned to Sysmex, describes and claims a reagent preparing apparatus. The Sysmex patent describes that it is possible to prepare a reagent at a desired dilution by mixing a predetermined reagent with pure water. Verification that the reagent concentration is standard may done by measuring the electrical conductance of the manufactured reagent. However, the patent also recognizes that erroneous analysis results may still be obtained and seeks to improve the reliability of reagent preparing apparatus. The Sysmex patent thus describes an apparatus that includes a reagent preparing section for preparing a diluted reagent containing a predetermined reagent and pure water; an electrical conductivity measuring section for measuring electrical conductivity of the diluted reagent prepared by the reagent preparing section, and a pH measuring section for measuring hydrogen ion concentration of the diluted reagent prepared by the reagent preparing section. The apparatus also uses a controller for performing predetermined processing, the controller configured to stop supply of the diluted reagent to the sample measuring section when the electrical conductivity measured by the electrical conductivity measuring section or the hydrogen ion concentration is outside predetermined ranges. Commercially available Sysmex® XN-Series™ Hematology Analyzers use the commercially available Sysmex® RU-20 Concentrated Reagent Delivery System to deliver a constant supply of Diluent from concentrate. One box of concentrate is equivalent to 25 boxes of standard Diluent.

Sysmex also describes an alternate system in its U.S. Pat. No. 9,164,021. This system uses a series of diluting chambers, diaphragm pumps, stirring chambers, and supply chambers and requires the use of positive and negative pressure pumps.

Both of these Sysmex systems are highly complicated and can be subject to various technical breakdowns. They do not address all of the problems that may be experienced with reducing the number of diluent containers that may be needed for analytic laboratory equipment.

BRIEF SUMMARY

Embodiments of the invention described herein thus provide systems and methods for diluent preparation modules and diluent preparation units, either or both of which deliver Diluent to an analytic instrument. The disclosed Diluent Preparation Module (DPM) prepares Diluent from purified water (PW or W) and reagent concentrate (RC or C). Use of the DPM system reduces the number of times that cubes of pre-prepared Diluent must be replaced. For example, a lab with multiple DxH instruments, reporting 2800 CBC/DIFF results per day, requires about 18 ten-liter cubes of pre-prepared Diluent per day. The present disclosure replaces the use of pre-prepared Diluent with a DPM that prepares the Diluent from purified water and reagent concentrate, which means that only a single ten-liter cube of reagent concentrate must be used (and exchanged) per day. As background, each 10 L cube is over 10 kg (22 pounds), so it is much easier for laboratory personnel using the analytic equipment to change only one cube per day instead of eighteen cubes.

Another aspect relates to a Diluent Preparation Unit (DPU) to supply Diluted Reagent Concentrate to one or more Analytic Instruments, wherein the DPU comprises two or more Diluent Preparation Modules (DPMs), which may be referred to as a first DPM (DPM1) and a second DPM (DPM2). Each Diluent Preparation Module is as described herein, but the aspect of combing two or more DPMs into a redundant DPU Unit gives the system a means, when one DPM reports failure, to quickly switch to the other DPM before the analytic instrument(s) are impacted by (e.g., consume any significant amount of) unacceptable quality prepared Diluent from the first DPM.

A further aspect relates to a DPU used to supply Diluent to one or more analytic instruments and to systems for such supply. The first DPM and the second DPM collectively form a Unit (DPU). The DPU is configured using available software and electronic signal technology. When the first DPM is close to being depleted of reagent concentrate, the first DPM is automatically taken off-line, and Diluent from the second DPM is directed to the one or more analytic instruments. The Unit (DPU) may give a notification to laboratory personnel to substitute a full container of reagent concentrate for the depleted container of reagent concentrate in the first DPM. Similarly, when the second DPM is close to being depleted of reagent concentrate, the second DPM is automatically taken off-line, and Diluent from the first DPM is directed to one or more analytic instruments and a similar notification may be given, with this back-and-forth replenishing of depleted reagent concentrate continuing as long as the Diluent Preparation Unit is in operation.

In certain examples, there is provided a Diluent Preparation Module comprising: a system for combining liquids from two separate sources into a combiner feature to provide a mixed liquid, wherein there is no air access between the separate sources or the combiner feature; a system for moving the mixed liquid into a single reservoir, and a system for moving the mixed liquid from the single reservoir into one or more analytic instruments. The combiner feature may be a T-connector or a Y-connecter. The liquids from the two separate sources may be purified water from a water purifier system and reagent concentrate from a reagent concentrate container. The mixed liquids may be Diluent. The system may mix the liquids in a downward then upward direction to create a U-trap configuration of liquid flow so that any unmixed reagent concentrate that sinks into this path will be captured by the U-trap. The reservoir may be formed as a debubble chamber comprising an inclined pipe. There may be one or more corrugated pulse suppressor structures associated with a conduit that delivers at least one of the liquids to the combiner feature.

A specific embodiment provides an integrated Liquid Analyzer Calibration System. At least one Liquid Analyzer may be positioned in the inlet port to the reservoir, in the reservoir, in the exit port of the reservoir, or combinations thereof. The Liquid Analyzer may be a conductivity meter(s), pH meter(s), refractometer(s), hydrometer(s), osmometer(s), or combination thereof. It is also possible to use a dual head pump to move liquid from a first source and liquid from a second source into the combiner feature.

Another example provides a Diluent Preparation Module comprising: a combiner feature for combining liquids without allowing air access to the liquids during mixing; a first conduit and a first pump for delivering purified water from a source of purified water to the combiner feature; a second conduit and a second pump for delivering reagent concentrate from a reagent concentrate container to the combiner feature; wherein the combiner feature mixes the purified water and the reagent concentrate to provide a Diluent; a third conduit comprising a mixing pipe for delivering the Diluent to a reservoir, the reservoir comprising a debubbler chamber; and a system for delivering the Diluent from the reservoir to one or more analytic instruments requiring the Diluent. This system may have a liquid trap downstream of the combiner feature for capturing any unmixed reagent concentrate from the Diluent. The source of purified water may provide water substantially airfree, and it is possible for the system to leave out valves controlling the forward motion of each liquid while flowing toward the reservoir, and wherein there is no air access between the source of the purified water, the reagent concentrate container, the combiner feature, and the reservoir.

Another example may provide a Diluent Preparation Module with a Liquid Analyzer Calibration System that has means of draining the Liquid Analyzer (i.e., draining the reservoir if the Liquid Analyzer is within the reservoir); a means of moving Liquid Analyzer Standard from a container of Liquid Analyzer Standard to the Liquid Analyzer (i.e. to the reservoir if the Liquid Analyzer is within the reservoir), and a means of calibrating the Liquid Analyzer using the Liquid Analyzer Standard.

Another example may provide two or more Diluent Preparation Modules described, forming a Diluent Preparation Unit.

There is also provided a method for supplying a flow of Diluent to one or more analytic instruments through a Diluent Preparation Unit (DPU), wherein the DPU comprises a first Diluent Preparation Module (DPM1) and a second Diluent Preparation Module (DPM2), the method comprising when DPM1 is close to being depleted of reagent concentrate, automatically taking DPM1 off-line, directing Diluent from DPM2 to the one or more analytic instruments, giving a notification to laboratory personnel to substitute a full container of reagent concentrate for the depleted container of reagent concentrate of DPM1; and wherein when DPM2 is close to being depleted of reagent concentrate, automatically taking DPM2 off-line, directing Diluent from DPM1 to the one or more analytic instruments, giving a notification to laboratory personnel to substitute a full container of reagent concentrate for the depleted container of reagent concentrate in the DPM2. This back-and-forth replenishing of depleted reagent concentrate occurs while the analytic instruments are online.

There is also provided a method for supplying a flow of Diluent to one or more analytic instruments through a Diluent Preparation Unit (DPU), wherein the DPU comprises a first Diluent Preparation Module (DPM1) and a second Diluent Preparation Module (DPM2), the method comprising: if DPM1 detects failure to produce adequate quality or quantity of diluent, automatically taking DPM1 off-line, directing Diluent from DPM2 to the one or more analytic instruments, and giving a notification to laboratory personnel about the DPM1 failure; and if DPM2 detects failure to produce adequate quality or quantity of diluent, automatically taking DPM2 off-line, directing Diluent from DPM1 to the one or more analytic instruments, and giving a notification to laboratory personnel about the DPM2 failure. This method may occur while the analytic instruments remain online.

BRIEF DESCRIPTION OF THE DRAWINGS

FIG. 1 shows a schematic view of a T-connector used to combined flow paths of purified water and reagent concentrate to produce Diluent.

FIGS. 2A-2C show three different examples of the flow paths used to combine purified water and reagent concentrate to produce Diluent.

FIG. 4A shows a Reservoir Pump Truth Table, which shows the way in which each fluidic function in the calibration process is achieved.

FIG. 5A shows a Reservoir Pump Truth Table, which shows the way in which each fluidic function in the calibration process achieved.

DETAILED DESCRIPTION

Figure 3:
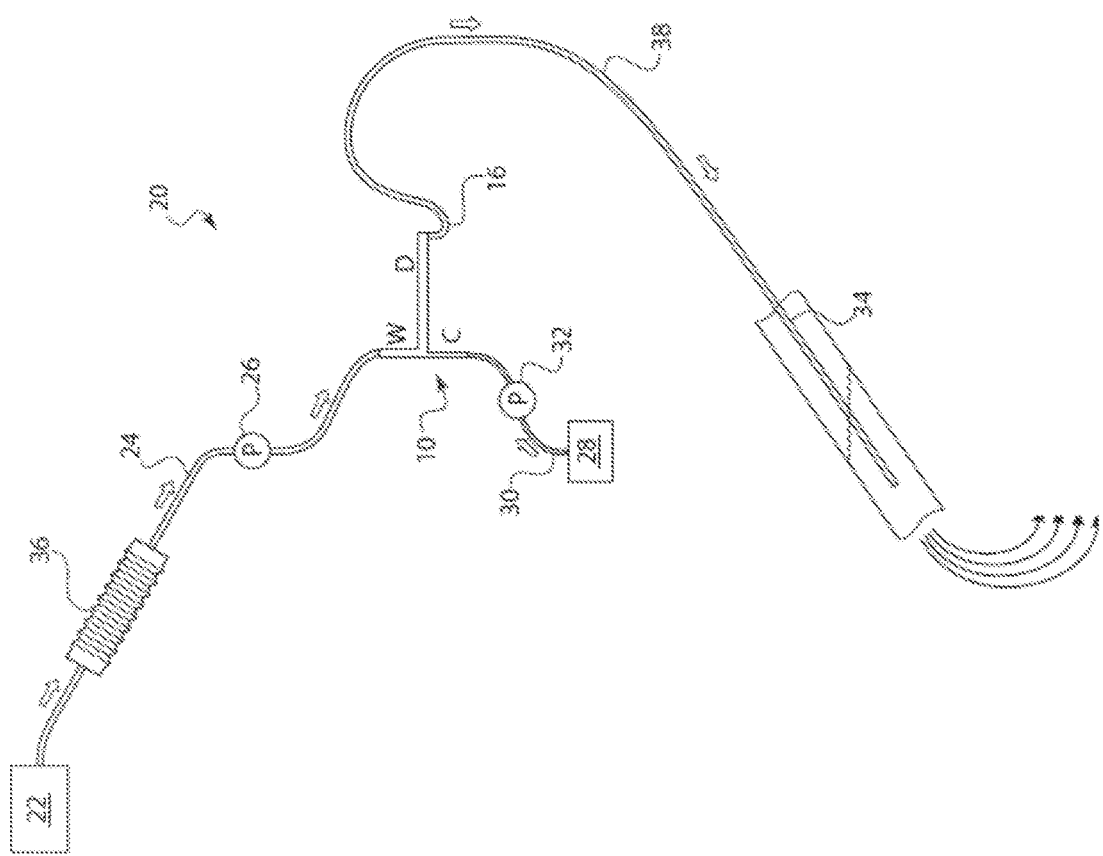
FIG. 3 shows a schematic of fluid flow through one embodiment of a Diluent Preparation Module (DPM) disclosed.

Embodiments of the present disclosure provide a system for combining purified water and reagent concentrate in order to provide a Diluent for use in medical analysis laboratory equipment (also referred to analytic instruments or as "analyzers" in the figures). The system may be referred to herein as a Diluent Preparation Module ("DPM"). One or more DPMs may be combined for collective use, and may be referred to as a Diluent Preparation Unit ("DPU"). The DPU may be associated with one or more analytic instruments in order to supply Diluent prepared thereto.

Certain examples of the medical analysis laboratory equipment/analytic instruments process and analyze patient samples in order to determine cell or particle count, morphology, and other data. During processing and analysis, it is generally desirable to prevent fluidic bubbles or microbubbles from flowing through the equipment, because extraneous bubbles may be recognized by the equipment and counted as cells or particles, resulting in erroneous results. For example, if microbubbles were to reach the analytic laboratory instruments, the microbubbles could cause platelet background issues, i.e., the microbubbles could mistakenly be counted as platelets by the instruments. Accordingly, one embodiment of the disclosed system includes a chamber that traps bubbles. In one example, there is provided a de-bubble chamber that allows microbubbles in the prepared Diluent to float away before they are introduced into any instruments.

Another embodiment provides a conductivity probe that ensures that the Diluent is mixed properly. This can provide a quality check or feedback loop. If there is a problem with one of the Diluent Preparation Modules (DPM), redundancy of the system provides at least a second DPM that may be used to prepare the Diluent instead. The DPM includes both (a) a conductivity probe (a.k.a. a Liquid Analyzer or Liquid Analyzer sensor) that constantly checks and ensures the quality of the prepared Diluent, as well as (b) an onboard conductivity standard, referred to as a Liquid Analyzer standard. The onboard conductivity standard is a container of solution that has a known "assay" or "calibration" value. The Liquid Analyzer standard is used to check and recalibrate (if needed) the conductivity probe. Other systems that seek to prepare diluent on site do not incorporate such an onboard conductivity standard. The conductivity standard ensures accuracy of the DPM conductivity probe readings. This calibration check can be set to be automatic. In one example, the calibration check occurs in the background, on a schedule (which may be once per day, once per week, or set at any other appropriate interval).

A further aspect of the disclosed DPM is its simplicity. A specific example disclosed requires only three pumps, two valves, one chamber, and no compressor (no pneumatic vacuum or pressure required). By comparison, competitor units use two pumps, twenty three valves, six chambers, and a compressor (a source of pneumatic vacuum and pressure is required). Simplifying the DPM system provides a greater reliability and lesser potential maintenance expenses or down time.

A further aspect of the disclosed DPM system is its redundancy. In specific examples, each workcell (which is generally a collection of two, three, or four instruments) is provided with two Diluent Preparation Modules, which are collectively referred to as a Diluent Preparation Unit (DPU). The redundancy of two complete DPMs provides the workcell with improved instrument uptime and a better backup plan. If a DPM within a workcell fails (referred to as the first DPM or DPM1), the workcell automatically continues to operate at full throughput by switching to a second DPM (or DPM2) connected with the workcell. This prevents the laboratory personnel from having to switch all of the workcells back to using pre-prepared diluent, which is how currently available systems operate.

A further aspect of the disclosed DPM is its combination of liquids from two separate sources into combiner feature. In specific examples, the combiner feature may be a T-connector or a Y-connector. The combined liquids are then moved into a reservoir and then into one or more analytic instruments. The mixed liquids may be moved via a combination of pumps, valves, and tubing. The mixed liquids may move via gravity feed. It is also possible to use vacuum and/or pressure sources, although not required. In specific embodiments, there is no air access between the source of the purified water and the source of the reagent concentrate and the reservoir. The combiner feature provide air tight or airless mixing.

In use, the Diluent Preparation Module (DPM) consistently mixes Reagent Concentrate ("RC" or "C") and Purified Water ("PW" or "W") in the correct proportions to form "diluted Reagent Concentrate" which is referred to herein as "Diluent." After the DPM mixes Reagent Concentrate and Purified Water into Diluent, the Diluent is then supplied to one or more analytic instruments. The Diluent that is supplied by the DPM has been found to be equivalent in quality and performance to the existing ready-to-use Diluent (also referred to herein as "pre-prepared diluent"). The Diluent matches in all respects the requirements of an analytic instrument.

A further aspect of the disclosed DPM provides a liquid trap. As background, Reagent Concentrate has a higher density than the density of the Purified Water. A mixture of the two liquids has a density between the two. In one embodiment, there is provided a flow path geometry that uses the differences of densities to minimize uncontrolled mixing, in the wrong proportions, of the Purified Water and the Reagent Concentrate. For example, in order to minimize the fluids mixing in an uncontrolled manner in the wrong proportions when the DPM is idle, the Purified Water flow (W) can be configured to point downward into the combining T or combining Y. The Reagent Concentrate flow (C) can be configured to point upward into the comber feature (e.g., combining T or combining Y). The Purified Water tends to float upward back into itself, and the Reagent Concentrate tends to sink downward back into itself. The liquid trap is designed in a "U" or a curved shape, such that when the combined flow of the two mixed liquids exits the combining T or Y, first in a downward direction then upwards to create a U-trap configuration of liquid flow, any concentrate that sinks into this path will be captured by the U-trap. This configuration minimizes uncontrolled mixing and diffusion of the Purified Water, Reagent Concentrate and the combined liquids into each other during idle non flow times.

Referring now to FIG. 1, there is shown a schematic illustration of a combiner feature 10 configured for use in connection with a Diluent Preparation Module (DPM) described herein. The combiner feature 10 is configured to join purified water W with reagent concentrate C. The combiner feature 10 is illustrated as defining a T-connector shape, wherein purified water W is moved into the combiner feature 10 from an upward to downward direction as illustrated by arrow 12. Reagent concentrate C is moved into the combiner feature 10 from a downward to upward direction as illustrated by arrow 14. Reagent concentrate C has a higher density than purified water W, so the purified water W entering downward tends to float back into itself and the reagent concentrate C entering upward tends to sink back into itself. Accordingly, delivering the reagent concentrate C at an entry point that is lower than the entry point of the purified water W can help provide more consistent mixing of the fluids to form the Diluent. After passing the combiner feature 10, the liquids are mixed into a Diluent that enters a liquid trap 16 via a conduit portion 18 that carries the mixed fluids.

The liquid trap 16 is illustrated as a U-shaped trap. In use, the U-shaped liquid trap 16 captures any reagent concentrate C that sinks down into the Diluent path D.

FIGS. 2A-2C illustrate alternate embodiments of a combiner feature 10. Although the figures illustrate alternate combiner feature 10 configurations, in each instance, tubing carrying the reagent concentrate C points upward into the T-connector or the Y-connector, and tubing carrying the purified water W points downward into the connector.

In FIG. 2A, the combiner feature 10 joins purified water W that enters the combiner feature 10 downward and at an angle into the combining T combiner feature 10. The reagent concentrate C is directed upward at an angle into the combining T combiner feature 10. The combined fluids are then directed to the liquid trap 16 via conduit portion 18. FIG. 2B illustrates a similar concept having a differently-shaped combining Y combiner feature 10. In this example, purified water W is directed into the connector in an upward to downward direction, and reagent concentrate C is directed into the connector at an upward and inward angle. FIG. 2C illustrates another similar concept having a differently-shaped combining Y combiner feature 10. In this example, purified water W is directed into the connector in a V-shaped conduit, and reagent concentrate C is directed into the connector in a downward to upward direction. Again, the fluids are mixed in a conduit portion 18 that leads to the liquid trap 16.

The conduit portion 18 may be integral with or connect at a connection point with a diluent path D that leads the mixed Diluent to the liquid trap 16. In each of the schematics shown, the liquid trap 16 directs liquid flow in a downward direction then upwards, which creates a U-trap configuration shape. The U-trap configuration of liquid flow causes any reagent concentrate that sinks into the path to be captured by the U-trap configuration. This configuration minimizes uncontrolled mixing and diffusion of the purified water W, the reagent concentrate C, and the combined liquids into each other during idle non-flow times.

In summary, FIG. 2 shows three different examples of the flow paths used to combine the purified water W and reagent concentrate C to produce Diluent. The combiner feature 10 may be a combining T, a combining Y, or any other appropriate geometry. Because the purified water W and Diluent path D carry larger volumes at faster flowrates as compared to the reagent concentrate C pathway, the diameter of the reagent concentrate C pathway may accordingly be sized smaller than the diameters of the purified water W and Diluent path D.

FIG. 3 shows a fluidic schematic of an embodiment of an individual Diluent Preparation Module (DPM) 20. As shown, purified water W is delivered from a water purifier system 22 to the combiner feature 10 via fluid conduit 24. The water purifier system 22 may be any appropriate water purifying system or purified water source. A water pump 26 may be used to force water through the fluid conduit 24 to deliver the purified water W to the combiner feature 10. In some embodiments, it has been found that running the purified water W through a corrugated pulse suppressor 36 can help reduce or prevent bubbles. A bubble removing reservoir is also described below, but removing bubbles early in the process can also be advantageous.

As also shown, reagent concentrate C is delivered from a reagent concentrate container 28 to the combiner feature 10 via fluid conduit 30. A reagent pump 32 (similar to the water pump 26) may be used to force water through the fluid conduit 30 to the combiner feature 10. As shown, the purified water W and the reagent concentrate C meet and are combined at the combiner feature 10. The combined fluids result in Diluent. The Diluent is sent through the liquid trap 16 and leaves via conduit 38, for delivery to a reservoir 34. Diluent may be held in reservoir 34 until its use is needed by one or more instruments.

Figure 4:
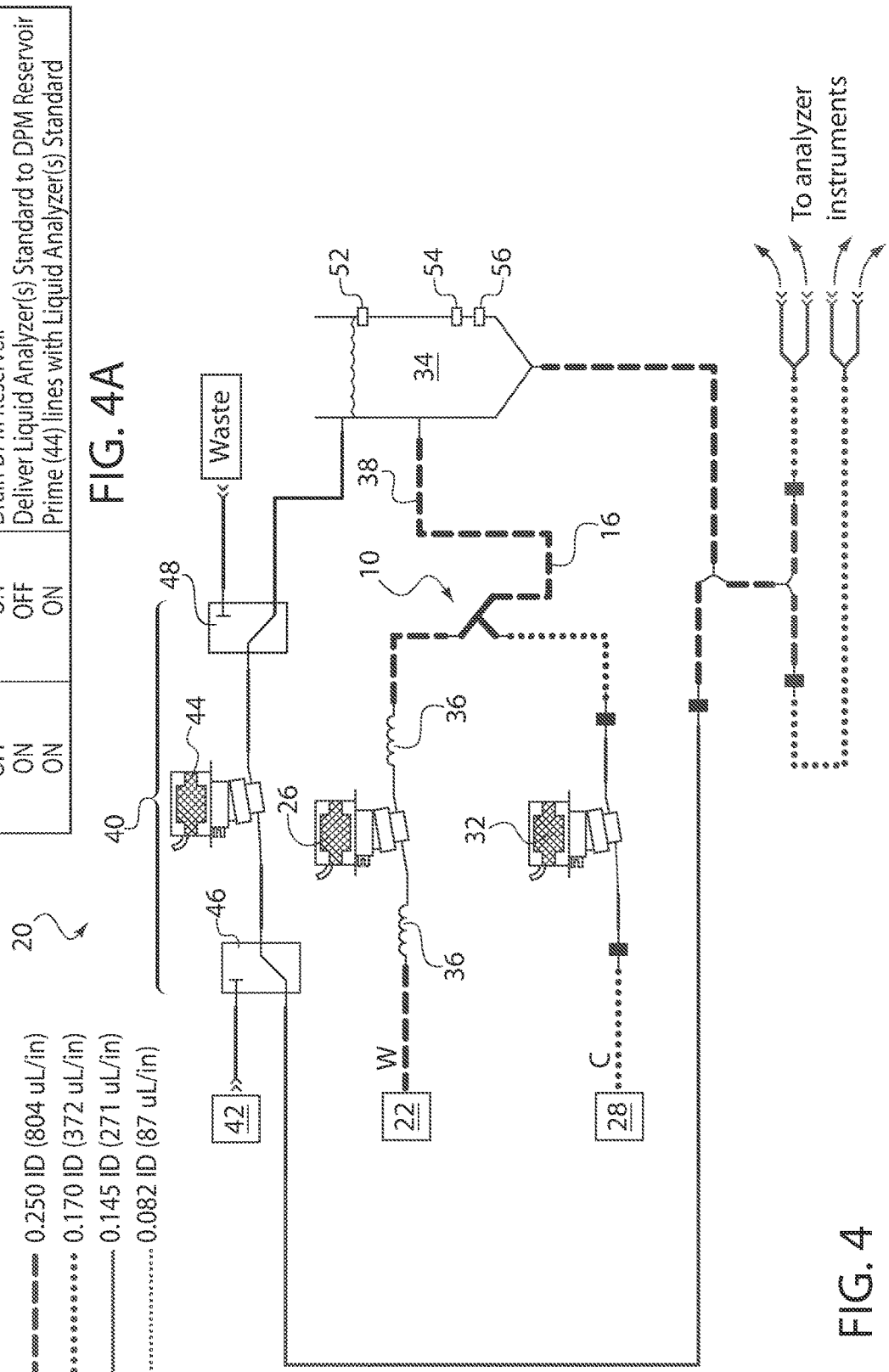
FIG. 4 shows a DPM Fluidic Schematic of an embodiment of an individual Diluent Preparation Module.
Figure 5:
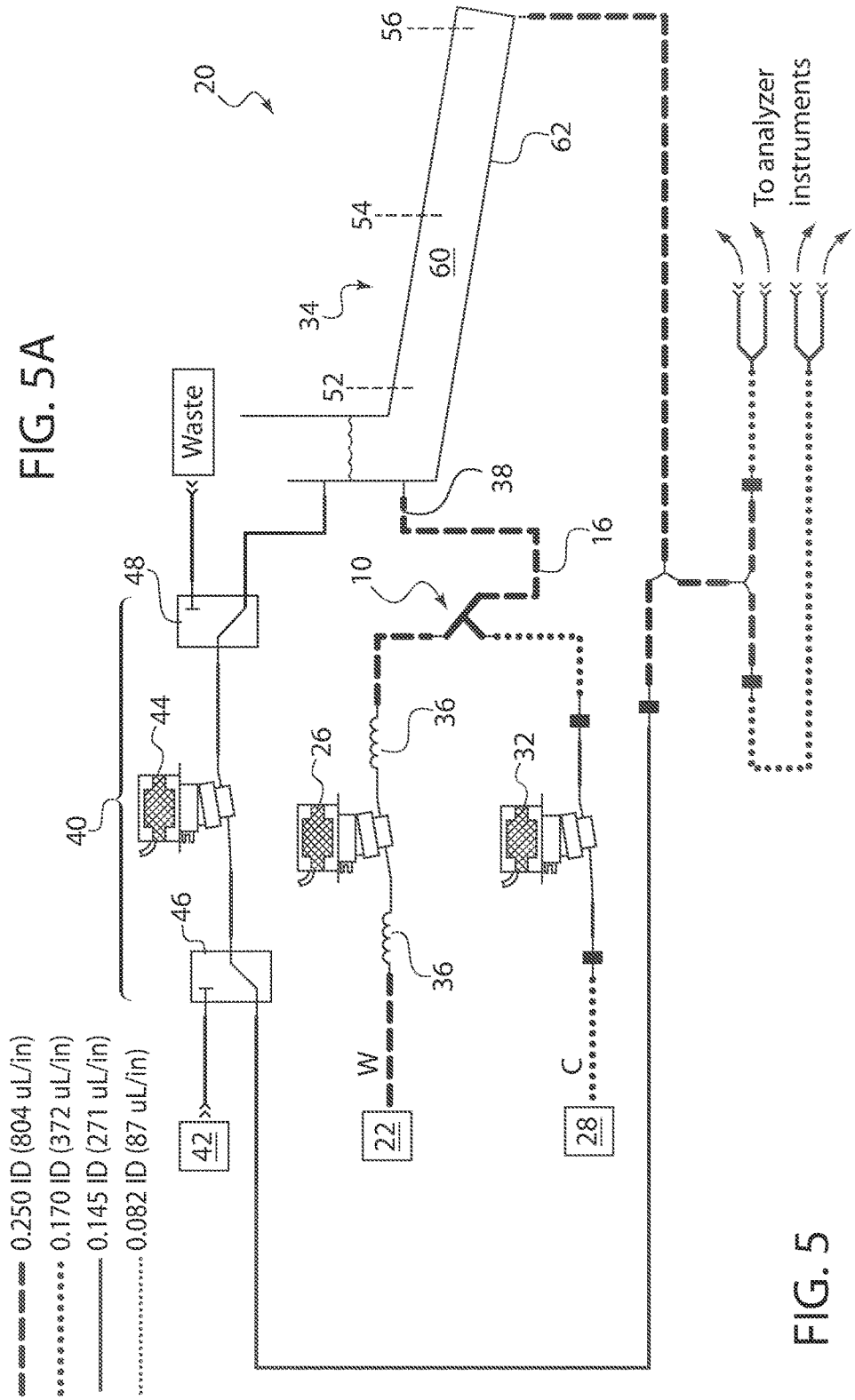
FIG. 5 shows a DPM Fluidic Schematic of another embodiment of an individual Diluent Preparation Module.

FIGS. 4 and 5 illustrate fluidic schematics of the DPM 20 in more detail. Similar to the schematic of FIG. 3, FIGS. 4 and 5 show that the purified water pump 26 receives its purified water W from a water purifier system 22, and the reagent concentrate pump 32 receives it reagent concentrate C from a reagent concentrate container 28. The output of the two pumps is combined in a combiner feature 10 and exits the connector into a mixing pipe or conduit 38. The mixing pipe 38 delivers the Diluent to a reservoir 34. FIG. 4 illustrates one option of a shape for reservoir 34. FIG. 5 illustrates an alternate option of a shape for reservoir. In FIG. 5, the reservoir functions as a debubbler chamber (shown in more detail in FIG. 6, and as will be described in more detail below).

The reservoir 34 may be provided with one or more sensors 50. In the example illustrated by FIG. 4, the reservoir 34 has at least one upper sensor 52 that is configured to indicate a "full level." The reservoir 34 also has at least one lower sensor 54 that is configured to indicate a "low level." It is possible for more than one upper sensor 52 and more than one lower sensor 54 to be provided around various portions of the reservoir 34. The reservoir 34 is also provided with at least one liquid analyzer sensor 56. The liquid analyzer sensor 56 communicates with the Liquid Analyzer Calibration System 40 as outlined below.

The main job of liquid analyzer sensor 56 is to read the Diluent and ensure the quality of the Diluent. Additionally, the liquid analyzer sensor 56 may read the "Liquid Analyzer Standard" in order to ensure that the liquid analyzer sensor 56 is calibrated correctly and providing accurate readings.

Part of the simplicity of the disclosed system is that the Liquid Analyzer is located in the reservoir. Competitor systems use an inline liquid analyzer in the path (transferring into a chamber or recirculating back into a chamber)—being able to analyze in the reservoir is an advantage.

FIGS. 4 and 5 illustrate a Liquid Analyzer Calibration System 40 that may be used to test/calibrate the DPM 20. The Liquid Analyzer Calibration System 40 is used to check and recalibrate (if needed) the liquid analyzer sensor 56. As with other systems, the DPM includes a conductivity probe that constantly checks and ensures the quality of the prepared Diluent. However, in addition, the DPM also includes an onboard conductivity standard (a liquid in a container) that is used to check and recalibrate (if needed) its conductivity probe. Other systems that seek to prepare diluent on site do not incorporate such an onboard Liquid Analyzer standard. This Liquid Analyzer standard ensures the accuracy of the liquid analyzer sensor readings. This calibration check can be set to be automatic. In one example, the calibration check occurs in the background, on a schedule (which may be once per day, once per week, or set at any other appropriate interval). Accordingly, while other reagent preparation systems may include liquid analyzer sensor(s) for measuring the reagent they prepare, they do not disclose a method for keeping their liquid analyzer sensor(s) calibrated.

The disclosed DPM provides the Liquid Analyzer Calibration System 40 as an onboard system. Although one Liquid Analyzer Calibration System 40 is illustrated, it should be understood that more than one Liquid Analyzer Calibration System 40 may be incorporated with the DPM 20.

In one embodiment, the method the Liquid Analyzer Calibration System 40 uses to check and/or calibrate the Liquid Analyzer sensor(s) 56 is as follows. With reference to FIGS. 4 and 5, the Liquid Analyzer Standard is a container 42 of liquid analyzer standard solution that has known "assay" or "calibration" values for the Liquid Analyzer(s). The overall process may include the following method:

(1) drain the reservoir 34 of any Diluent that may be contained therein;

(2) rinse the reservoir 34 (this may be done by priming the reservoir pump 44 with Liquid Analyzer standard, then partially filling the reservoir 34 with the Liquid Analyzer standard, then draining the reservoir 34);

(3) prime the reservoir pump 44 with Liquid Analyzer standard, then partially fill the reservoir 34 with Liquid Analyzer standard so that the liquid analyzer sensor(s) 56 are submerged; and 4) read and, as necessary, calibrate each Liquid Analyzer sensor 56.

Before beginning the calibration process above, if the reservoir 34 is in a production mode (where "production mode" means that the reservoir 34 can supply the Analytic Instrument(s) with Diluent), the reservoir 34 may exit the "production mode" and enter a "non-production mode," meaning the reservoir 34 cannot supply the Analytic Instrument(s) with Diluent. Once the calibration process is complete, the reservoir 34 is drained of the Liquid Analyzer standard and re-rinsed with Diluent for continued production. This calibration process ensures that the Diluent is mixed correctly. If a problem is identified with a particular DPM, it may be possible to switch to a secondary DPM that may be associated with the workcell.

FIGS. 4A and 5A provide a Reservoir Pump Truth Table, which shows the way in which each fluidic function in the calibration process described above is achieved. As background, the reservoir pump 44 may have two valves that create four reservoir pump inlet/outlet combinations. Both valves in an "OFF" status is an inactive "do nothing" fluidic process where the reservoir pump 44 is not turned on. The three active fluidic processes in which the reservoir pump 44 is turned on are: "Drain Reservoir," "Deliver Liquid Analyzer(s) Standard to Reservoir," and "Prime Reservoir Pump with Liquid Analyzer(s) Standard." For example, the reservoir 34 is drained by turning off first valve 46 (which selects the reservoir's drain port as the pump's inlet) and turning on a second valve 48 (which directs the pump's outlet to "waste"). The "waste" location may be a waste drain in the lab or "waste" may be delivered to a waste container. To drain the reservoir 34 completely, the reservoir pump 44 is run with the valves in this state for a set volume or time after the low-level sensor 54 in the reservoir 34 detects air.

FIG. 5 shows a DPM Fluidic Schematic of an embodiment that has an alternate reservoir. The reservoir of FIG. 5 is a debubbler chamber 60. In one example, the chamber 60 is designed as an inclined pipe 62 that facilitates the removal of embedded bubbles within the fluids.

As background for the addition of a debubbler chamber 60, when the DPM is in operation, it is desirable to reduce the presence of bubbles within the fluids because bubbles, including microbubbles, can be counted as red blood cells, white blood cells, or platelets by the analytic instruments, leading to erroneous readings. The main error of concern is microbubbles causing abnormally high platelet counts.

Figure 6:
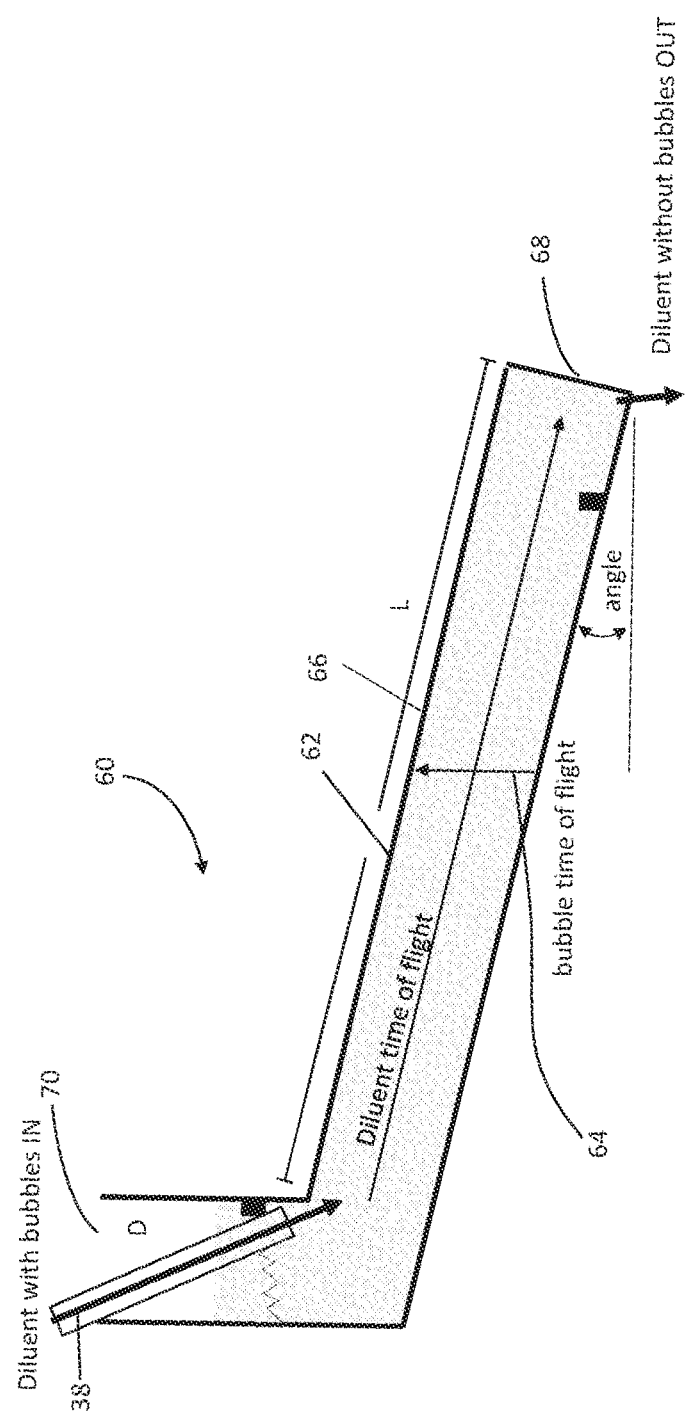
FIG. 6 shows the outline of a section of inclined pipe configured to separate bubbles from the Diluent liquid.

FIG. 6 shows a cross-sectional schematic of a section of inclined pipe 62 that is configured to separate bubbles from the Diluent liquid contained therein. As is shown, the conduit 38 to the reservoir/chamber is designed to enter the debubbler chamber 60 such that the Diluent is delivered below liquid level, although toward the high end of the chamber 60. This can be beneficial in order to prevent the introduction of additional air bubbles (by entering below liquid level) but also allowing bubbles to have the full length of the inclined pipe 62 in order to rise out of the Diluent.

The debubbling section of the inclined pipe 62 is at a slight angle (in some examples, about 10 to 30 degrees) with respect to horizontal. The length L of this section is greater than the diameter of the pipe 62. The way this section of inclined pipe 62 functions is that the maximum vertical 64 distance that the bubbles must float upward to reach the ceiling 66 of the pipe and thus be "safe" (meaning that bubbles do not exit with the fluid at the exit 68 of the pipe) is shorter than the distance that the fluid must travel from its point of injection into the pipe to the exit 68 of the pipe. Thus, although the fluid may travel significantly faster than the speed at which bubbles would float upward, the bubbles still "win the race" and reach the ceiling 66 of the pipe rather of exiting with the fluid at the exit 68 of the pipe. Another reason that the debubbler chamber 60 has a section of inclined pipe 62 that is angled relative to the horizontal is so that bubbles that reach the ceiling 66 of the pipe 62 may accumulate and then creep upward and exit the pipe at its upper end 70.

A debubbling section of pipe forming a debubbler chamber 60 is most effective when the fluid's minimum time of flight is greater than the bubbles' maximum time of flight. It can be appreciated that the cross sectional shape of the debubbling section of pipe may not be round, rather, the debubbling section of pipe may be more efficient at debubbling if the cross-sectional shape is shorter than it is wide. For example, a suitable debubbling section could comprise a cross-sectional shape that is a rectangle (sometimes referred to as a rounded rectangular shape) with rounded corners, with the pipe being about 3 to 5 times shorter than it is wide.

For illustrative purposes, the table below compares three different cross sectional geometries for inclined pipe 62. All three geometries have the same cross sectional area (5.07 cm²). The cross sectional geometry of the first column is round (with a 2.54 cm diameter). The cross sectional geometry of the second column has an aspect ratio of approximately two (3.38 cm wide/1.5 cm high). The cross sectional geometry of the third column has an aspect ratio of approximately five (5.07 cm wide/1.0 cm high). As the cross sectional aspect ratio becomes greater, the inclined pipe becomes more efficient at debubbling (as shown in the last two rows of the table, debubbling can be accomplished with a shorter length and a lower volume).

|  |  |  | 438.00 | mL/min | max prepared diluent flowrate |
|  |  |  | 0.20 | cm/s | bubble float rate |
|  |  |  | 5.07 | cm^2 | cross sectional area |
|  |  |  | 1.44 | cm/s | prepared diluent avg speed |
|  |  |  | 20 | deg | angle (from horizontal) |
| round | rectangle | rectangle |  |  | cross sectional shape |
| 2.54 |  |  |  | cm | debubble dia |
| 2.54 | 1.5 | 1.0 |  | cm | cross sectional height |
| 2.54 | 3.38 | 5.07 |  | cm | cosss sectional width |
| 2.70 | 1.60 | 1.06 |  | cm | bubble float height |
| 13.5 | 8.0 | 5.3 |  | s | max bubble time of flight |
| 19.47 | 11.50 | 7.67 |  | cm | min debubble length |
| 98.7 | 58.3 | 38.8 |  | mL | debubble volume |

As illustrated by the schematic of FIG. 3, the addition of commercially available "pulsation suppressors" (corrugated tubing 36, such as Teflon tubing) at the water pump inlet and/or outlet can reduce pulsation and bubbles caused by pulsation. It should be understood that such tubing 36 may be positioned anywhere along the conduit line as deemed necessary or beneficial. Fluidic formation of microbubbles can also be reduced by (a) ensuring the source of purified water is degassed, meaning it has as little dissolved gas in it as possible;

(b) fluidic geometry design, meaning, among other engineering designs, having no air access between the source of the purified water and the source of the reagent concentrate and the reservoir; and (c) when the DPM is in Diluent production mode, no draining and re-priming of pumps should take place.

Degassed purified water is purified water with minimal dissolved gas. Degassed purified water, when stored in a vented container, will seek equilibrium with the gas above it and eventually the purified water will become 100% saturated with the gas above it. Thus, it is beneficial to store degassed purified water without allowing it to contact any gas. One such suitable storage vessel for degassed purified water is an airfree bladder (or a substantially airfree purified water source).

Purified water is typically supplied meeting one or more of the following quality requirements:

Conductivity <1 μS/cm, same as Resistivity >1 MΩ-cm

Bacterial <1 cfu/mL

TOC <50 ppb

Filter <0.2 μm

Degassed.

Reagent concentrate is supplied by the manufacturer and is chosen to meet the needs of the analytic instrument in which the reagent is intended to be used. For example, COULTER® DxH™ Diluent, available from Beckman Coulter, is a commercially available isotonic buffered Diluent in conjunction with a cyanide-free lytic agent for counting and sizing blood cells on the workcell, and is used with the DxH® 2401 Hematology Analyzer.

The means for moving liquids throughout the DPM and combining liquids as described can be any type of known fluid movement device, including but not limited to pumps, impellers, any other appropriate liquid-moving device, or any combination thereof. Different configurations of pumps can be used including forward motion and suction pumps. The number of pumps can be adjusted to provide the desired flow patterns.

In an embodiment, the means for combining liquids are one or more pumps and wherein the set flow rate and/or precise volume for each pump is selected to provide the desired precise ratio between the purified water and Reagent Concentrate and the set flow rate for each pump is also selected so that the purified water and Reagent Concentrate undergo mixerless in-line mixing.

In one embodiment, two pumps are used to operate the disclosed DPM 20. One pump is used to move the purified water (referred to as the water pump 26), and one pump is used to move the reagent concentrate (referred to as the reagent pump 32). The two pumps also drive the combined solution, given the name "Diluent," from the combiner feature 10 to the reservoir 34. Flow exiting the combiner feature 10 is equal to the sum of the flows entering the combiner feature 10.

An alternate option that is equivalent to the two pumps is to use a "dual head" pump. In this example, one pump head pumps purified water and the other pump head pumps reagent concentrate.

Typically, each Analytic Instrument provides its own means for moving the Diluent from the reservoir 34 into the Analytic Instrument. This means for moving the Diluent could be a vacuum source or the Analytic Instrument's own pump(s).

Figure 7:
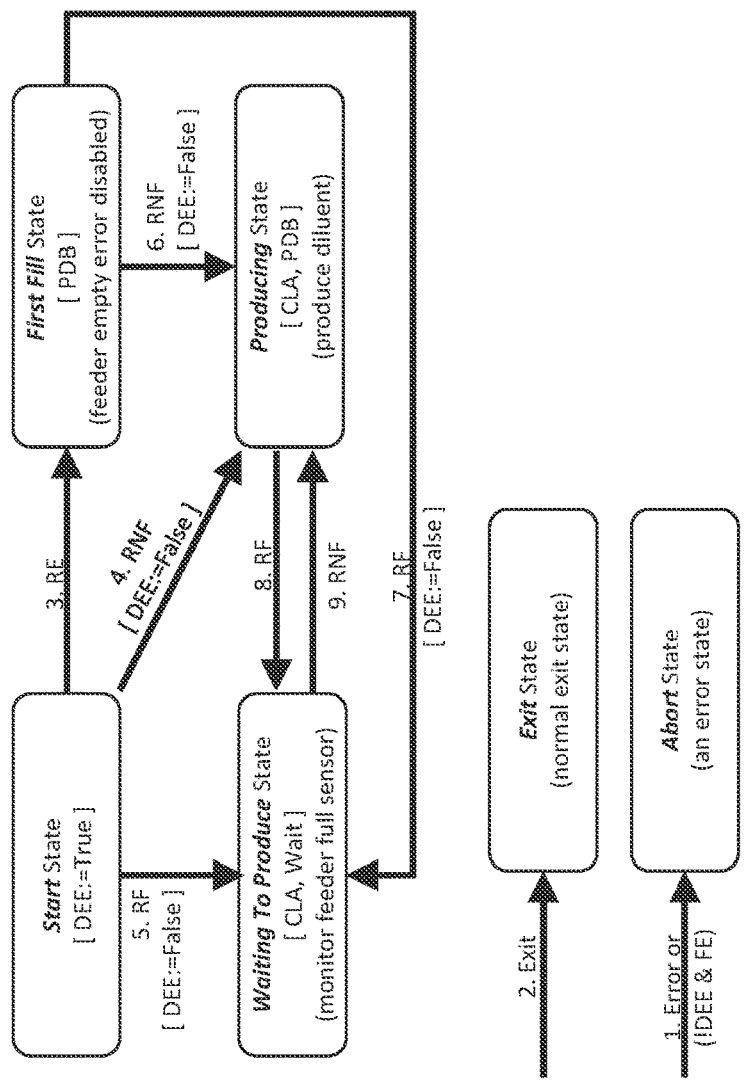
FIG. 7 shows the DPM Prepare Diluent State Machine which shows the "Control Logic Pattern" for each different status of the machine.

FIG. 7 illustrates the state of the machine instructions that control the production of Diluent. As shown, Diluent is produced in the following manner: While the DPM is "online" in Diluent production mode, only two pumps are used, the purified water pump and the reagent concentrate pump. In order to meet the demand consumption of Diluent of the Analytic Instrument(s), the two pumps are turned on, simultaneously, for short periods of time. Each short period of time is called a batch. In other examples, a dual head pump serves this function, such that only one pump is used. FIG. 7 shows the control—when to produce another batch of Diluent versus when to remain idle—while in Diluent production mode. The reservoir has three statuses based on two level sensors. The two-level sensors are the upper level sensor (the "reservoir full" level sensor) and the lower level sensor (the "reservoir low" level sensor). Each level sensor can detect liquid or air. The three statuses of the reservoir are: "reservoir full (RF)" when the full level sensor detects liquid (indicating that fluid in the reservoir is at or above the full level sensor); "reservoir not full (RNF)" when the full level sensor detects air and the low level sensor detects liquid (indicating that fluid in the reservoir is below the full level sensor and above the low level sensor); and "reservoir empty" (RE) when both level sensors detect air (indicating that fluid in the reservoir is below the low level sensor, so the reservoir may not be completely empty, but the reservoir may no longer be able to safely supply the Analytic Instrument(s) with Diluent). The "reservoir empty" status usually triggers an error condition, although there are times, such as when the state machine is first starting, where it is normal or acceptable for the reservoir to have a "reservoir empty" status.

The reservoir has a number of states. During the majority of the time while in Diluent production mode, the reservoir alternates between the "Waiting-To-Produce" state and the "Producing" state. For those times when the reservoir is in a "Producing" state, the "Producing" state performs two state actions: "check Liquid Analyzer(s)," which means that the Liquid Analyzer(s) will be checked once to assure that the Diluent in the reservoir is of acceptable quality; and "produce Diluent batch," which means that one batch of Diluent will be produced. Then the full level and low-level sensors will be read to determine the reservoir status.

When the reservoir status is "reservoir not full," the reservoir will remain in the "Producing" state and perform each of the state actions again, i.e. "check Liquid Analyzer(s)" and "produce Diluent batch." Alternately, if the reservoir status is "reservoir full," then the reservoir will transition from the "Producing" state to the "Waiting to Produce" state via transition branch 8.

As background, the "test/calibrate" and "check and/or calibrate" use the "liquid analyzer sensor" 56 to read the liquid analyzer standard; these are the calibrations that are done perhaps once a day or once a week or at periodic set intervals. In the above description of the state machine, the "check Liquid Analyzer(s)" step means that the "liquid analyzer sensor" 56 is used to read the diluent in order to verify "that the Diluent in the reservoir is of acceptable quality." This Diluent quality check is done often (e.g., once every batch, whenever a new batch is produced, during short intervals (perhaps every half second) when the DPM is "Waiting to Produce," or any other appropriate programmed instances).

The "Waiting-To-Produce" state performs two state actions: "check Liquid Analyzer(s)" and "Wait." "Wait" means to do nothing for a short period of time, i.e. do nothing for half a second. Once the state actions are complete, the full and low-level sensors are read again to determine the reservoir status. When the level in the reservoir remains above the full level sensor, the reservoir status remains "reservoir full," and the reservoir remains in the "Waiting-To-Produce" state while it performs that state's two state actions again. As Analytic Instrument(s) consume Diluent, eventually the level in the reservoir drops and the full level sensor detects air instead of liquid. In this instance, the reservoir status becomes "reservoir not full," and the reservoir transitions from the "Waiting-To-Produce" state to the "Producing" state via transition branch 9.

Figure 8:
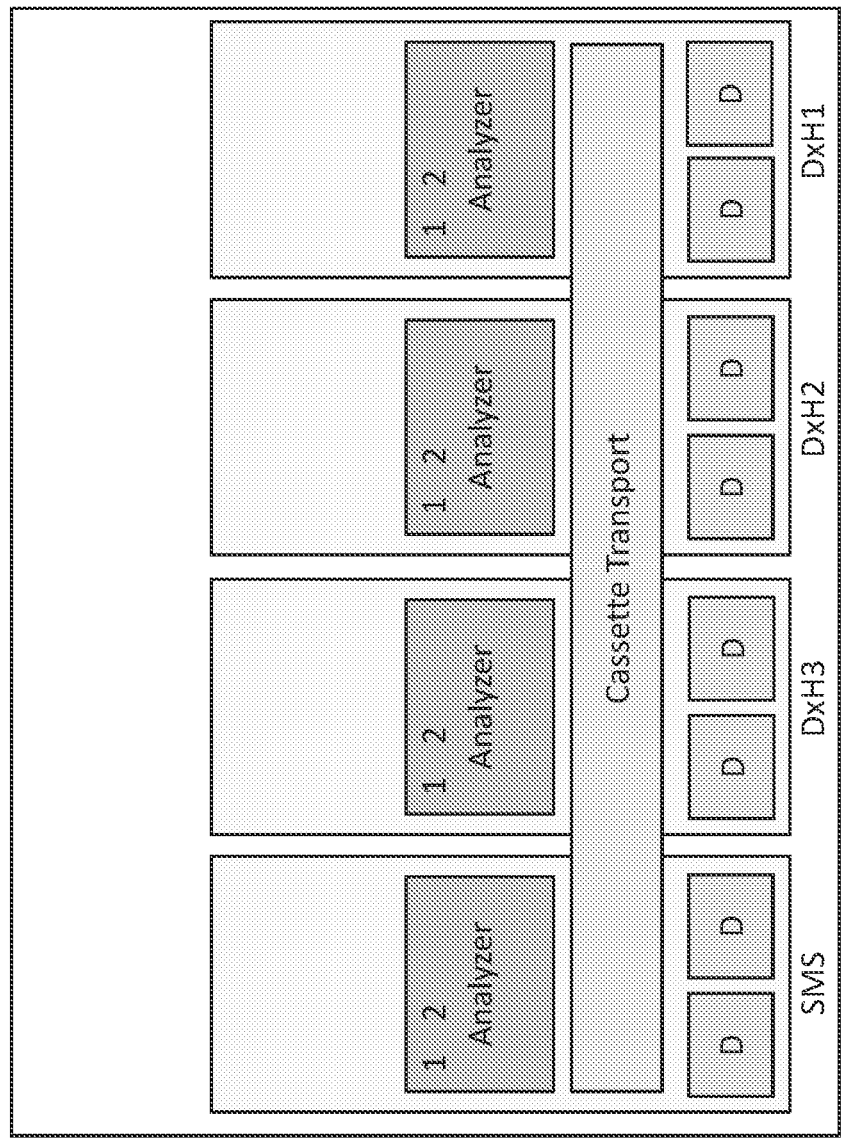
FIG. 8 shows an existing prior art system with one or more analyzers, without a Diluent Preparation Unit. Each analyzer uses two containers of ready-to-use Diluent.

FIG. 8 shows an existing system with a plurality of medical analysis equipment or analytic instruments, labeled as "analyzers." The existing system does not contain a Diluent Preparation Unit (DPU) nor any Diluent Preparation Modules (DPMs). Each analyzer in the system uses two containers of ready-to-use Diluent ("D"). When one container of Diluent D is depleted, the system automatically switches to the other container of Diluent while remaining online. The system notifies the user of the depleted container of Diluent, and the user may replace the depleted container with a new container of Diluent while the system remains online.

Figure 9:
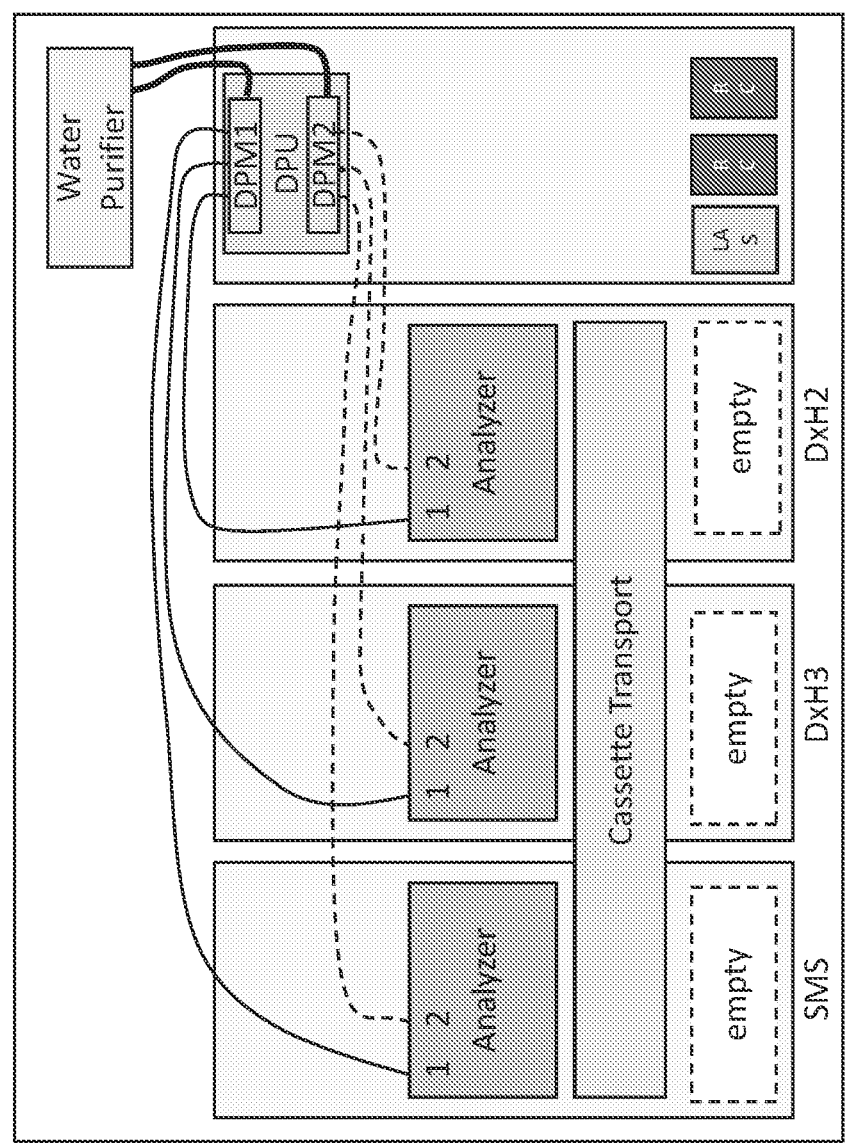
FIG. 9 shows an embodiment of a Diluent Preparation Unit positioned external to a system containing one or more analyzer(s). The Diluent Preparation Unit contains at least two or more Diluent Preparation Modules where each Diluent Preparation Module supplies Diluent to all analyzers in the system.
Figure 10:
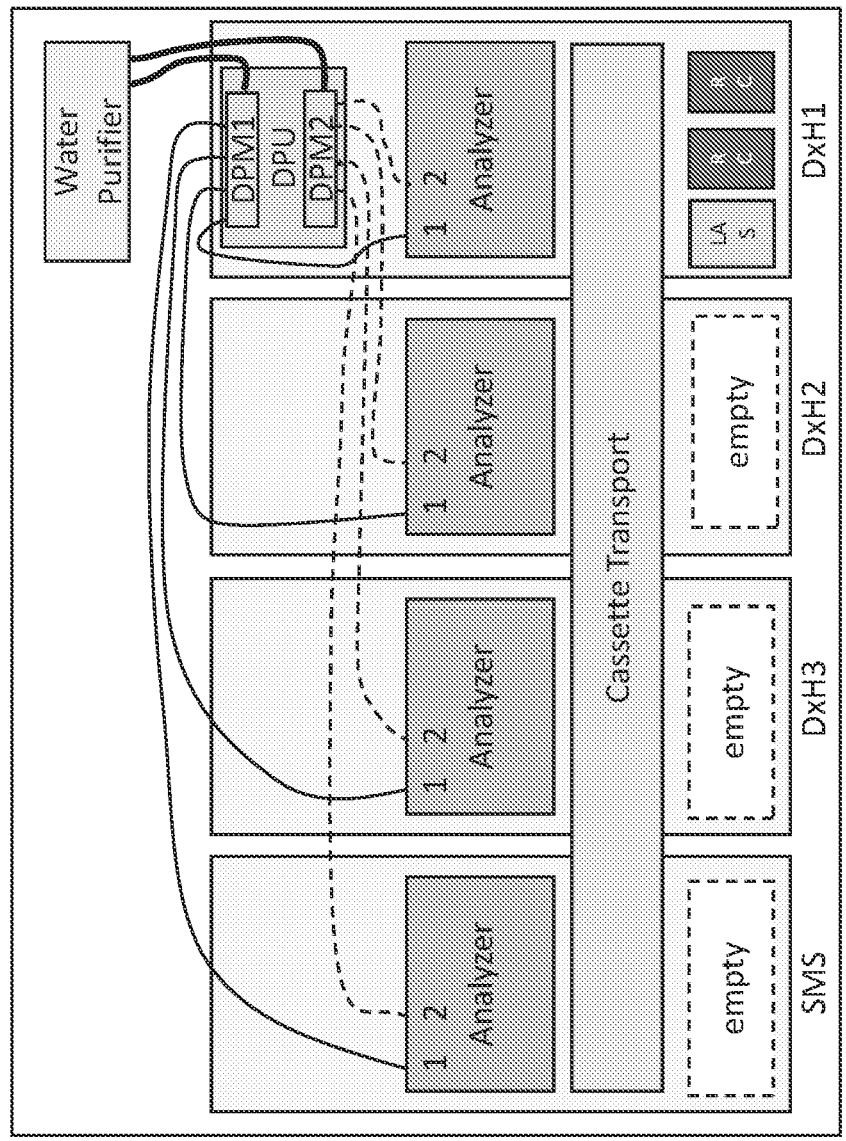
FIG. 10 shows an embodiment of a Diluent Preparation Unit positioned internal to a single analyzer. The Diluent Preparation Unit contains at least two or more Diluent Preparation Modules where each Diluent Preparation Module supplies Diluent to all analyzers in the system.
Figure 11:
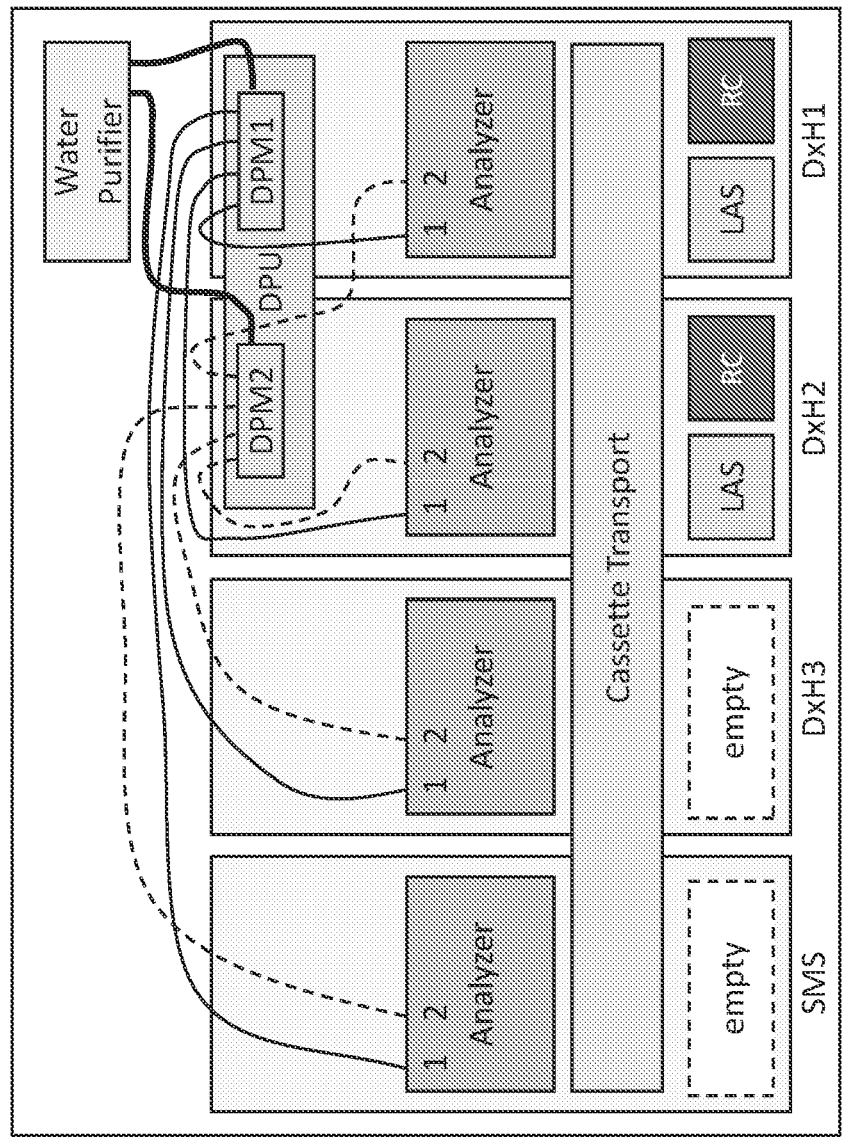
FIG. 11 shows an embodiment of a Diluent Preparation Unit partitioned across multiple analyzers. The Diluent Preparation Unit contains two or more Diluent Preparation Modules. Each Diluent Preparation Module supplies Diluent to all of the analyzers in the system.

FIGS. 9, 10, and 11 show various configurations of systems with a Diluent Preparation Unit (DPU). There are benefits to having a redundant system that provides more than one DPM, such as being able to switch between DPMs.

FIG. 9 shows a system with a plurality of analyzers using at least one Diluent Preparation Unit (DPU) that is external to all analyzers. In the example shown, two DPMs are provided (DPM1 and DPM2), but it should be understood that additional DPMs may be included as well. Each DPM supplies Diluent to all analyzers in the System. Each DPM uses a single container of Reagent Concentrate (RC). (Practically, in use, fluid lines connect the DPM to the RC/LAS, but because these connections are understood by this disclosure, they have not been included on the drawings to prevent undue confusion in the figures.) The DPU uses a single container of Liquid Analyzer(s) Standard (LAS) that is shared with all the DPMs. If one DPM fails, the degraded state of the System works from one container of Reagent Concentrate (RC) with no ability to automatically switch to a new container of Reagent Concentrate while online. This degraded state starts automatically (without user intervention) upon DPM failure.

FIG. 10 shows a system with a plurality of analyzers using a Diluent Preparation Unit (DPU) that is internal to a single analyzer. The system contains a DPU comprising two or more DPMs, DPM1 and DPM2. Each DPM supplies Diluent to all analyzers in the system. Each DPM uses a single container of Reagent Concentrate. The DPU uses a single container of Liquid Analyzer(s) Standard that is shared with all the DPMs. If one DPM fails, the degraded state of the system works from one container of Reagent Concentrate with no ability to automatically switch to a new container of Reagent Concentrate while online. This degraded state starts automatically (without user intervention) upon DPM failure. (A "degraded state" means that a system is not able to work at 100% of its capacity due to something being broken or some prerequisite not being met.)

(As background, being able to replace a depleted reagent while staying online is a benefit. However, the value of the benefit changes depending upon how often reagent needs to be replaced. For example, on systems that use ready-to-use diluent offered in 10 L diluent cubes, one container may provide enough diluent for 160 cycles. If the instrument runs 90 cycles/hour, under peak load, the instrument consumes the 10 L diluent cube in less than two hours. In this example, remaining online while replacing those 10 L ready-to-use diluent containers is significant. On the other hand, for all the other reagent containers (other than diluent), each reagent container may last for about 1000 or more cycles. It is more acceptable to go offline in order to replace these types of reagents. For 18× reagent concentrate, 18×160=2880 cycles per container. This is a situation in which it is acceptable to have to go offline in order to change the reagent, even if it is preferable to be able to remain online).

The redundancy of providing more than one DPM per workcell is an advantage. Each workcell of two, three, or four instruments is provided with two Diluent Preparation Modules (to form a DPU), which provides the workcell with improved instrument uptime and a better backup plan. If one DPM within a workcell fails, the workcell automatically continues to operate at full throughput using labor-saving concentrated diluent. For other systems without redundancy, the user is forced to manually switch all the workcell's instruments back to the more labor-intensive un-concentrated diluent, provided in individual containers.

FIG. 11 shows a system with two or more analyzers using a Diluent Preparation Unit (DPU) internal to the system, with the DPU partitioned across multiple analyzers. The system contains a DPU comprising two or more DPMs, each analyzer containing at most one DPM. In one example, one analyzer has a first DPM (DPM1) and a second analyzer has a second DPM (DPM2). Each DPM supplies Diluent to all analyzers in the system. Each DPM uses a single container of Reagent Concentrate and a single container of Liquid Analyzer(s) Standard. If one DPM fails, the degraded state of the system works from one container of Reagent Concentrate with no ability to automatically switch to a new container of Reagent Concentrate while online. This degraded state starts automatically (without user intervention) upon DPM failure.

Figure 12:
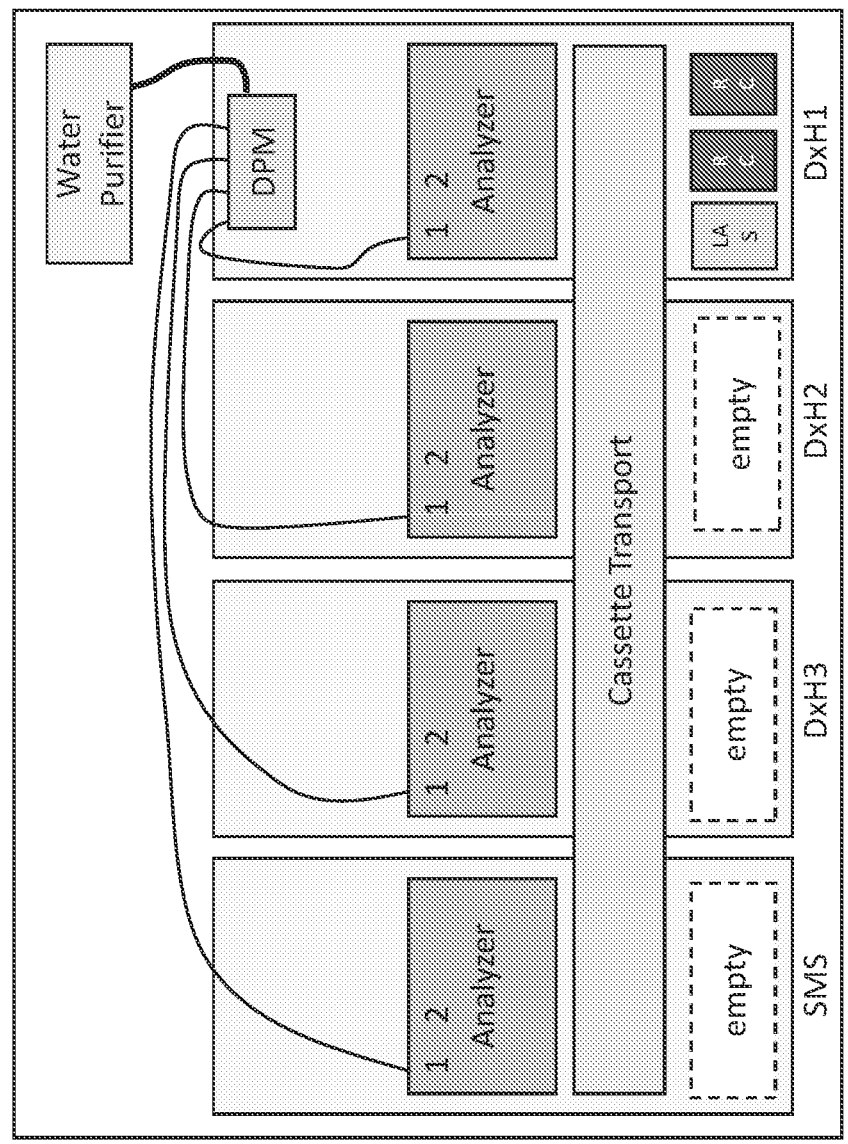
FIG. 12 shows an embodiment of a system containing one or more analyzers and a Diluent Preparation Module.

FIG. 12 shows a system with a plurality of analyzers using a Diluent Preparation Module (DPM) with two containers of Reagent Concentrate. The system contains a DPM. The DPM supplies Diluent to all analyzers in the system. The DPM is a DPM embodiment that uses two containers of Reagent Concentrate and a single container of Liquid Analyzer(s) Standard. When one container of Reagent Concentrate is depleted, the system automatically switches to the other container of Reagent Concentrate while remaining online, and the user may replace the depleted container with a new container of Reagent Concentrate while the system remains online. If the DPM fails, the system goes offline and the system cannot go back online until after the DPM's failure is resolved and the DPM is properly functioning. In this figure, each analyzer's second Diluent supply inlet is left unconnected/unused in this configuration.

Figure 13:
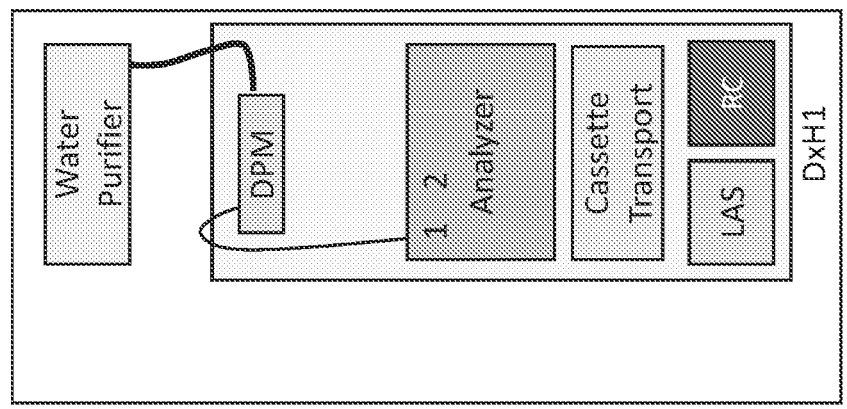
FIG. 13 shows an embodiment of a system containing an analyzer and a Diluent Preparation Module.

FIG. 13 shows a system with a single analyzer using a single Diluent Preparation Module (DPM). The DPM supplies Diluent to the analyzer. The DPM uses a single container of Reagent Concentrate and a single container of Liquid Analyzer(s) Standard. When the container of Reagent Concentrate is depleted, the system goes offline, and the system cannot go back online until after the user replaces the depleted container with a new container of Reagent Concentrate. If the DPM fails, the system goes offline, and the system cannot go back online until after the DPM's failure is resolved and the DPM is properly functioning. In this figure, the analyzer's second Diluent supply inlet is left unconnected/unused in this configuration.

In any of these examples, it may be possible to configure the system to allow the operator to switch containers while remaining on line.

In many of the Figures, more than one DPM is used, to form a Diluent Preparation Unit (DPU). The DPU is thus a self-sustained unit, connected to power and purified water, which may be positioned external to an analytic instrument(s) or which may be positioned internal within the analytic instrument(s). The DPU comprises at least two Diluent Preparation Modules (DPMs). One DPM may be referred to as a first DPM (DPM1) and a second DPM may be referred to as a second DPM (DPM2). The DPU may functionally provide these, and other, benefits:
1) Online switching of Reagent Concentrate cubes;
2) Redundancy (emergency backup mode for failure of one DPM; the unit can continue to use Reagent Concentrate in the other DPM; as an alternative to switching to "ready-to-use" Diluent or going offline);
3) Better lot-to-lot traceability. While the analytic instrument(s) remain online, provides the DPM (that is not supplying Analytic Instruments with Diluent) a chance to completely flush out old lot number prepared Diluent and replace it with new lot number prepared Reagent Concentrate without the Analytic Instruments having to consume a mixture of two lot numbers;
4) While the analytic instrument(s) remain online, provides the DPM (that is not supplying Analytic Instruments with Diluent) a chance to check and/or recalibrate its "Liquid Analyzer sensor(s)"; and
5) While the analytic instrument(s) remain online, provides the DPM (that is not supplying Analytic Instruments with Diluent) a chance to check and/or recalibrate the ratio of Purified Water to Reagent Concentrate.

The Analytic Instrument(s) may include, but is(are) not limited to, hematology analyzer(s), stain makers, urinalysis machines, or any other analyzer intended to receive and output data based on a fluid sample. One design of a Diluent Preparation Unit could stand next to the workcell to reconstitute Reagent Concentrate to working strength Diluent.

The DPU may be used to supply Diluent to one or more analytic instruments, and this disclosure also relates to systems for such supply. For example, at least a first DPM and at least a second DPM collectively form a Unit (DPU). More than two DPMs are possible for use in a unit as additional DPMs are considered within the scope of this disclosure. The DPU is configured using available software and electronic signal technology. When the first DPM (DPM1) is close to being depleted of reagent concentrate, the first DPM is automatically taken off-line, and Diluent from the second DPM (DPM2) is directed to the one or more analytic instruments. The Unit (DPU) may give a notification to laboratory personnel to substitute a full container of reagent concentrate for the depleted container of reagent concentrate in the first DPM (DPM1). Similarly, when the second DPM (DPM2) is close to being depleted of reagent concentrate, the second DPM is automatically taken off-line, and Diluent from the first DPM is directed to one or more analytic instruments and a similar notification may be given, with this back-and-forth replenishing of depleted reagent concentrate continuing as long as the Diluent Preparation Unit is in operation.

In summary, as compared to existing equipment that supplies diluted reagent by mixing water with concentrated reagent, the disclosed Diluent Preparation Module ("DPM") uses a single chamber (in a single DPM) to hold and present the prepared Diluent. "Present" means supply the prepared Diluent to the analytic instrument(s) that consume the prepared Diluent. Other systems may have a minimum of two chambers for prepared reagent: one chamber for "non-validated" prepared reagent (where the prepared reagent may or may not be of acceptable quality) and a second "validated" reagent chamber. Prepared reagent only passes from the "non-validated" to the "validated" reagent chamber if it passes a quality test. The "validated" reagent chamber (or some chamber after it) supplies the prepared reagent to the analytic instrument(s). One possible advantage of the disclosed DPM's single chamber system is that it is simpler (and therefore likely to have fewer parts and be less costly and more robust/reliable).

Additionally, the disclosed DPM uses a quick, single stage, open loop method to combine the purified water and concentrated reagent. Other systems use an iterative (usually multi-stage), closed loop feedback method to combine the water and reagent concentrate. The DPM's single stage open loop method is faster and simpler (i.e. has fewer steps) than a closed loop iterative method. The DPM uses precise flow rates and/or volumes to achieve quality prepared Diluent on the first try, and expects success on the first try. The DPM uses its "Liquid Analyzer" (i.e. conductivity meter) to verify quality of prepared Diluent success and to detect failure of quality of prepared Diluent, but the DPM fully expects to achieve quality of prepared Diluent on the first try with high reliability. The Diluent Preparation Unit (redundancy of DPM modules) gives the system a way, if one DPM reports failure, to quickly switch to the other DPM before the analyzer instrument(s) are impacted by (consume any significant amount of) unacceptable quality prepared Diluent from the first DPM.

Additional features that may distinguish the disclosed DPM from existing technology are its:
  single stage volumetric dilution (not multistage);
  final stage internal Liquid Analyzer(s) only (not a feedback loop);
  in-line mixing (no mix tank) or mix tank contains stirrer and Liquid Analyzer(s) (does not recirculate to an external Liquid Analyzer(s) that is separate from the DPM reservoir);
  no storage tank is required. Diluent production is stored in a small volume reservoir where the production rate of the DPM surpasses/keeps up with Diluent consumption without need for a large buffer volume (in some examples, the maximum volume of Diluent in the DPM reservoir may be about 225 mL);
  on board, automated control and/or calibration of one or more of the Liquid Analyzer(s). This contrasts with and is an improvement over existing technology where the Liquid Analyzer(s) can drift out of calibration without the system becoming aware that the Liquid Analyzer(s) are out of calibration, and therefore there was a risk that the quality of Diluent could be measured as acceptable when the quality of the Diluent was unacceptable. On board, automated control and/or calibration mitigates this risk.
  extraction tank that does not need recirculation or stirring.
    Volume is small/used quickly compared to a 10 L Diluent cube, so stagnation is not a concern.
    No large volumes allow for better Diluent lot number traceability (little lot-to-lot mixing)
  Internal Liquid Analyzers (one or combination of any of the following)
    Temperature Compensated Conductivity (not temperature controlled conductivity)
    Osmolality (typically through freezing point measurement)
    pH
    Refractometer
    Hydrometer Regarding the volume of the reservoir, the dimension tables above provide examples of volume required for debubbling as 98.7 mL (round) down to 58 mL (2 to 1 aspect ratio) or 38 mL (5 to 1 aspect ratio). For comparison, one cycle of an analyzer instrument (e.g., a Beckman Coulter DxH 600/800/900) uses 60 mL. This instrument holds about 5 cycles (300 mL) onboard in its reservoirs and tubings. Some reagent preparation systems provide 5 L or 20 L in an onboard reservoir, which results in a high amount of lot-to-lot number mixing. The disclosed DPM reservoir uses only about 100 mL for debubbling (along with additional "buffer" volume). Its "full" level sensor may be positioned to detect a volume of about 180 mL level, with each batch being about 45 mL. The most full the reservoir becomes is one batch over the full sensor (about 225 mL, which is 180+45). In a specific example, the DPM reservoir may be about 300 mL, with the intention that it rarely if ever holds more than 225 mL liquid in it. This amount is well below the current reservoir sizes of 5 L or 20 L.

Regarding the Temperature Compensated Conductivity, typically, conductivity probes have a thermistor built-in. They measure conductivity and temperature and then "compensate" the conductivity reading (calculate according to a model) and report out a "conductivity at standard temperature (i.e., 25° C.). Some systems use temperature control. They bring the prepared diluent to a target temperature and then measure its conductivity, which is done to obtain a "truer" measurement. Temperature control requires a Peltier to heat or cool the prepared diluent (or sometimes just a heater). These components can complicate the system, add costs to the system, and it takes time and energy to heat and/or cool the prepared diluent. Systems that require use of a heater cannot operate on the hottest days of summer when the purified water is too warm. The lab must have "summer stock" of ready-to-use reagent for when the weather is too warm. Temperature characterization testing of the Temperature Compensated Conductivity Probe of the disclosed system has shown that the conductivity probe's temperature compensated readings are accurate throughout the Analytic Instruments' temperature operating range. For example, such characterization testing may be performed by forcing the conductivity standard to various temperature points throughout the temperature characterization range and at each temperature performing one or multiple temperature compensated readings with the conductivity probe. The testing passes if all reported "conductivity at standard temperature" measurements match the assay value of the conductivity standard within appropriate accuracy limits. This alleviates the need for cooling or heating the diluent for testing.

A first aspect provides a Diluent Preparation Module comprising: means for moving liquids and combining liquids from two separate sources into a T-connector and then further moving the mixed liquids into a reservoir, wherein the mixed liquids are moved from the reservoir into one or more Analytic Instruments by additional means for movement of liquid; wherein the means for moving liquids are selected from the group of pumps, vacuum and/or pressure sources, and wherein the first liquid is Purified Water and the second liquid is Reagent Concentrate, and wherein there is no air access between the source of the Purified Water and the source of the Reagent Concentrate and the reservoir.

A second aspect provides a Diluent Preparation Module wherein the Reagent Concentrate has a higher density than the density of the Purified Water and the mixture of the two liquids has a density between the two and wherein to minimize the fluids mixing uncontrolled, in the wrong proportions, during times when the Diluent Preparation Module is idle, the Purified Water flow points downward into the combining T and tends to float upward back into itself, the Reagent Concentrate flow points upward into the combining T and tends to sink downward back into itself, and the combined flow of the two mixed liquids exits the combining T, first in a downward direction then upwards to create a U-trap configuration of liquid flow so that any concentrate that sinks into this path will be captured by the U-trap, and wherein this configuration minimizes uncontrolled mixing and diffusion of the Purified Water, Reagent Concentrate and the combined liquids into each other during idle non-flow times.

In an embodiment, the Diluent Preparation Module contains Reagent concentrate wherein the Reagent concentrate has a higher density than the density of the purified water and the mixture of the two liquids has a density between the two and wherein to keep the fluids separate during times when the Diluent Preparation Module is not working, the Purified Water flow points downward into the combining T, the Reagent Concentrate flow points upward into the combining T and the combined flow of the two mixed liquids exists the combining T, first in a downward direction then upwards to create a U-trap configuration of liquid flow, and wherein this configuration reduces uncontrolled mixing, in the wrong proportions, of the purified water, reagent concentrate and the combined liquids from diffusing back into each other.

In an embodiment of the Diluent Preparation Module, the source of Purified Water is degassed, which means the purified water has as little dissolved gas in it as possible.

In an embodiment of the Diluent Preparation Module there is no air access between the source of the purified water and the source of the Reagent Concentrate and the reservoir.

In an embodiment of the Diluent Preparation Module there are no valves present controlling the forward motion of each liquid from the source of the liquid to the reservoir.

In an embodiment of the Diluent Preparation Module of further includes means for reducing the presence of bubbles within all liquids; wherein said means are focused on keeping the Reynold's number, defining laminar or turbulent flow, well within the range of laminar flow exclusively.

In an embodiment of the Diluent Preparation Module, the module includes at least two pumps; wherein the first pump moves purified water from the source of purified water, through the purified water pipe, into the T-connector pipe fitting of the Module, the second pump moves Reagent Concentrate from a source of Reagent Concentrate through the Reagent Concentrate Pipe into the T-connector pipe fitting of the Module, and wherein the exit pipe from the T-Connector is known as the mixing pipe and wherein the mixing pipe flows into the reservoir; wherein the set flow rate for each pump is selected to provide the desired precise ratio between the Purified Water and Reagent Concentrate and the set flow rate for each pump is also selected so that the purified water and Reagent Concentrate undergo mixerless in line mixing, wherein the source of purified water is degassed meaning the purified water contains as little dissolved gases as possible), and wherein there are no valves present controlling the forward motion of each liquid as it flows towards the reservoir and wherein there is no air access between the source of the purified water and the source of the Reagent Concentrate and the reservoir, wherein said reservoir has at least one inlet port and at least one exit port; wherein the liquid in the exit pipe from the T-Connector enters the reservoir through the inlet port and the liquid leaving the reservoir via the exit port through an exit pipe enters an Analytic Instrument; wherein Liquid Analyzers are present, as necessary, in the inlet port to the reservoir, in the reservoir itself and in the exit port of the reservoir; wherein the Liquid Analyzers present include, but are not limited to, conductivity meter(s), pH meter(s), refractometer(s) and hydrometer(s).

The feature of "no valves" present controlling the forward motion of each liquid as it flows towards the reservoir is about avoiding the creation of bubbles. Avoiding or removing bubbles is important for the high flow rate paths within the system (e.g., the water path, and the combined diluent path). Some valves (i.e. rocker valves) have a tortuous internal fluidic pathway that create bubbles when fluid is flowed through them quickly. (The concentrate reagent path is a low flow rate path, and use of a rocker valve in that flow path is unlikely to create bubbles in the concentrate reagent path.) Valves such as pinch valves or shear valves have a clean fluidic pathway—they do not create bubbles even at high flow rates. These valves may be used in the high flow rate paths.

In an embodiment, The Diluent Preparation Module further comprises a
   (a) means of draining the reservoir,
   (b) means of draining the Liquid Analyzer(s),
   (c) means of moving Liquid Analyzer(s) standard from a container of Liquid Analyzer(s) standard to the reservoir, and
   (d) a means of calibrating the Liquid Analyzer(s) using the Liquid Analyzer(s) standard.

Diluent may be supplied to the workcells of the Analytic Instruments meeting the following quality requirements:
   Background ≤25/0.1 mL counts particles
   Osmolality 325 to 345 mOsm/Kg
   Conductivity 19 to 20 mS/cm
   pH 6.8 to 7.2.

In one embodiment of the DPU disclosed, the Diluent Preparation Unit (redundancy of DPM modules) gives the system a means, when one DPM reports failure, to quickly switch to the other DPM before the instrument(s) are impacted by (consume any significant amount of) unacceptable quality prepared Diluent from the first DPM.

In an embodiment of the system that delivers Diluent to one or more analytic instruments using a DPU (more than one DPM), the Diluent Preparation Unit is located external to (i.e., "outside of") one or more Analytic Instruments.

In another embodiment of the system, the Diluent Preparation Unit is located internal to (i.e., "inside of") one or more Analytic Instruments.

In a further embodiment of the system, the system further comprises means for traceability of Diluent to the specific lot number of Reagent Concentrate.

In an embodiment of the system, the system further comprises a valve that is capable of stopping all flow of liquids into and out of the reservoir.

In the claims, as well as in the specification above, all transitional phrases such as "comprising," "including," "carrying," "having," "containing," "involving," "holding," and the like are to be understood to be open-ended, i.e. to mean including but not limited to. Only the transitional phrases "consisting of" and "consisting essentially of" shall be closed or semi-closed transitional phrases, respectively.

While several embodiments have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

It should be understood that various different features described herein may be used interchangeably with various embodiments. For example, if one feature is described with respect to particular example, it is understood that that same feature may be used with other examples as well.

Changes and modifications, additions and deletions may be made to the structures and methods recited above and shown in the drawings without departing from the scope or spirit of the disclosure or the following claims.

What is claimed is:

1. A diluent preparation system comprising:
   a concentrated reagent source supplying a concentrated reagent;
   a water source supplying water;
   a reservoir containing a mixture of the concentrated reagent and the water; and
   a measurement system configured to detect a quality component of the mixture, the measurement system comprising
      a sensor configured to detect the quality component, wherein the sensor is located in the reservoir, and
      a calibrator configured to perform a calibration protocol comprising calibrating the sensor with a calibration liquid while the sensor is located in the reservoir, wherein the calibration protocol comprises rinsing the reservoir with the calibration liquid, draining the calibration liquid from the reservoir, and then calibrating the sensor with the calibration liquid.

2. The diluent preparation system of claim 1, wherein the calibrator further comprises a reservoir pump and flowlines that fluidly connect the reservoir pump and the reservoir, wherein the calibration protocol further comprises priming the reservoir pump and the flowlines with the calibration liquid prior to the rinsing of the reservoir with the calibration liquid.

3. The diluent preparation system of claim 2, wherein calibration liquid is a liquid of a known conductivity, and wherein the quality component is a conductivity measurement.

4. The diluent preparation system of claim 1, wherein the concentrated reagent and the water are mixed to form the mixture prior to delivery to the reservoir.

5. The diluent preparation system of claim 4, wherein the concentrated reagent and the water are mixed in a T-connector to form the mixture prior to delivery to the reservoir.

6. The diluent preparation system of claim 1, wherein the reservoir is in fluid communication with a hematology analyzer instrument.

7. The diluent preparation system of claim 1, wherein the calibration protocol comprises reading a conductivity measurement of the calibration liquid with the sensor to determine if the sensor is accurate.

8. The diluent preparation system of claim 1, wherein the calibration liquid is onboard the diluent preparation system.

9. A diluent preparation system comprising:
   a concentrated reagent source supplying a concentrated reagent;
   a water source supplying water;
   a reservoir containing a mixture of the concentrated reagent and the water;
   a sensor configured to detect a quality component of the mixture, wherein the sensor is located in the reservoir; and
   a calibration system configured to perform a calibration protocol comprising calibrating the sensor with a calibration liquid while the sensor is located in the reservoir, wherein the calibration protocol comprises rinsing the reservoir with the calibration liquid, draining the calibration liquid from the reservoir, and then calibrating the sensor with the calibration liquid.

10. The diluent preparation system of claim 9, wherein the calibration system further comprises a reservoir pump and flowlines that fluidly connect the reservoir pump and the reservoir, wherein the calibration protocol further comprises priming the reservoir pump and the flowlines with the calibration liquid prior to the rinsing of the reservoir with the calibration liquid.

11. The diluent preparation system of claim 10, wherein the calibration liquid is a liquid of a known conductivity, and wherein the quality component is a conductivity measurement.

12. The diluent preparation system of claim 9, wherein the concentrated reagent and the water are mixed to form the mixture prior to delivery to the reservoir.

13. The diluent preparation system of claim 12, wherein the concentrated reagent and the water are mixed in a T-connector to form the mixture prior to delivery to the reservoir.

14. The diluent preparation system of claim 9, further comprising a water pump configured to supply the water to the reservoir, a reagent pump configured to supply the concentrated reagent to the reservoir, and a reservoir pump configured to supply a calibration liquid to the reservoir.

15. The diluent preparation system of claim 9, wherein the calibration protocol comprises reading a conductivity measurement of the calibration liquid with the sensor to determine if the sensor is accurate and adjusting the sensor if the sensor is inaccurate.

16. A diluent preparation system comprising:
- a reservoir in fluid communication with both a water source supplying water and a concentrated reagent source supplying a concentrated reagent;
- the reservoir including a sensor located in the reservoir configured to detect a quality component of a mixture contained in the reservoir; and
- a calibrator to perform a calibration protocol comprising calibrating the sensor with a calibration liquid while the sensor is located in the reservoir, wherein the calibration protocol comprises rinsing the reservoir with the calibration liquid, draining the calibration liquid from the reservoir, and then calibrating the sensor with the calibration liquid.

17. The diluent preparation system of claim 16, wherein the calibrator further comprises a reservoir pump and flowlines that fluidly connect the reservoir pump and the reservoir, wherein the calibration protocol further comprises priming the reservoir pump and the flowlines with the calibration liquid prior to the rinsing of the reservoir with the calibration liquid.

18. The diluent preparation system of claim 17, wherein the calibration liquid is a liquid of a known conductivity, and wherein the quality component is a conductivity measurement.

19. The diluent preparation system of claim 16, wherein the concentrated reagent and the water are mixed to form the mixture prior to delivery to the reservoir.

20. The diluent preparation system of claim 16, wherein the reservoir is in fluid communication with a hematology analyzer instrument.

* * * * *